US010822656B2

(12) United States Patent
Gigrich

(10) Patent No.: US 10,822,656 B2
(45) Date of Patent: Nov. 3, 2020

(54) METHODS AND SYSTEMS FOR HIGH-THROUGHPUT TOXICITY SCREENING OF A COMPOUND USING MAHALANOBIS VALUES

(71) Applicant: James Gigrich, Lorton, VA (US)

(72) Inventor: James Gigrich, Lorton, VA (US)

( * ) Notice: Subject to any disclaimer, the term of this patent is extended or adjusted under 35 U.S.C. 154(b) by 787 days.

(21) Appl. No.: 15/640,569

(22) Filed: Jul. 2, 2017

(65) Prior Publication Data

US 2019/0002975 A1    Jan. 3, 2019

(51) Int. Cl.
| | |
|---|---|
| *C12Q 1/6876* | (2018.01) |
| *G01N 33/50* | (2006.01) |
| *G16B 40/00* | (2019.01) |
| *G16C 20/30* | (2019.01) |
| *G16C 20/80* | (2019.01) |
| *G16B 25/10* | (2019.01) |

(52) U.S. Cl.
CPC ........ *C12Q 1/6876* (2013.01); *G01N 33/5014* (2013.01); *G01N 33/5067* (2013.01); *G16B 40/00* (2019.02); *G16C 20/30* (2019.02); *C12Q 2600/142* (2013.01); *C12Q 2600/158* (2013.01); *G16B 25/10* (2019.02); *G16C 20/80* (2019.02)

(58) Field of Classification Search
CPC ...... C12Q 1/6876; C16C 20/30; G16B 40/00; G01N 33/5014; G01N 33/5067
USPC .......................................................... 702/19
See application file for complete search history.

*Primary Examiner* — Jerry Lin
(74) *Attorney, Agent, or Firm* — Juneau & Mitchell; Todd L. Juneau

(57) ABSTRACT

The invention relates to methods and systems for high-throughput toxicity screening of compounds using Mahalanobis Values, and in particular comparing a normal unexposed transcriptome Mahalanobis Value in an in-vitro hepatocyte microassay against a calculated transcriptome Mahalanobis Value of hepatocytes exposed to a target compound for varying time periods and in varying concentrations.

11 Claims, 26 Drawing Sheets

Figure 12

| Categories | Different Models | | |
| --- | --- | --- | --- |
| | Animal-based Model | Tox21 | Hepatocyte Toxicogenomics Evaluation System |
| Model | Animal/Rodent Based | Chemical Structure Analysis | Human Hepatocytes |
| Cost | $1.5-3M | $8-20K | $8-20K |
| Time | Months to Years | Weeks to Months | Days to Weeks |
| Algorithm | Pathological | Pattern Matching Database–Toxicity Pathways | Mahalanobis Distance |
| Quick Screening | No | Yes- only 10,000 different compounds | Yes |
| # Animals per Compound | 100+ | Zero | Zero |
| Determine Risk Threshold Level | No | No | Yes |
| Dose Response | Apical | Apical | Dynamic Dose Response |
| Stress Response | Apical | Apical | Dynamic Stress Response |
| Type of Test | In-vivo | In-vitro | In-vitro |
| Efficiency | One compound one animal | Microarray-1K+ genes examined at once | Microarray – 1K+ genes examined at once |

Figure 14

Normal Observation Data

| Observation | Human | Time | AADAC | ABAT | ABAT | ABAT | ABCA1/P | ABCB1 | ABCB1 | ABCD3 | ABCD3 | ABHD1 | | ZNF423 |
|---|---|---|---|---|---|---|---|---|---|---|---|---|---|---|
| 1 | 1153 | 2 | 11.0256 | 7.19914 | 11.5739 | 12.195 | 1.94569 | 8.27264 | 10.2288 | 5.11241 | 9.71238 | 2.16769 | ...... | 2.54645 |
| 2 | 1153 | 6 | 10.884 | 7.1261 | 11.439 | 12.1621 | 2.19813 | 7.85822 | 9.80521 | 5.06597 | 9.8016 | 2.11619 | ...... | 2.34124 |
| 3 | 1153 | 12 | 10.7268 | 7.20991 | 11.5576 | 12.3101 | 2.14361 | 7.82711 | 9.6253 | 4.28068 | 9.96676 | 2.06155 | ...... | 2.56199 |
| 4 | 1153 | 24 | 10.7459 | 7.24696 | 11.2098 | 12.2521 | 1.96668 | 8.35191 | 10.6003 | 4.13006 | 9.88255 | 2.04756 | ...... | 2.08265 |
| 5 | 1153 | 72 | 10.7519 | 7.13002 | 11.4459 | 12.1975 | 2.19864 | 8.22659 | 10.5617 | 5.3585 | 9.89148 | 1.98987 | ...... | 2.55986 |
| 6 | 1154 | 2 | 11.378 | 6.80574 | 11.383 | 12.2301 | 2.20071 | 7.98964 | 9.36351 | 5.18838 | 9.99949 | 2.16893 | ...... | 2.27741 |
| 7 | 1154 | 6 | 11.2411 | 6.6179 | 11.3445 | 12.3665 | 2.36951 | 7.83606 | 8.98527 | 4.94545 | 10.0646 | 2.02351 | ...... | 2.48292 |
| 8 | 1154 | 12 | 11.4567 | 6.81031 | 11.3911 | 12.1197 | 2.29664 | 8.38575 | 9.03068 | 5.75146 | 10.0559 | 1.87863 | ...... | 2.47194 |
| 9 | 1154 | 24 | 11.2038 | 6.79729 | 11.5042 | 12.2708 | 1.94835 | 8.03032 | 9.61995 | 4.99484 | 10.2922 | 2.13269 | ...... | 2.08331 |
| 10 | 1154 | 72 | 11.0945 | 6.75036 | 11.5653 | 12.4734 | 1.96066 | 7.92116 | 9.95166 | 4.44589 | 10.0582 | 1.96847 | ...... | 2.26235 |
| 11 | 1156 | 2 | 11.8414 | 6.44791 | 11.2493 | 11.8724 | 2.21455 | 8.97211 | 9.49949 | 6.00563 | 10.0324 | 2.30087 | ...... | 2.26689 |
| 12 | 1156 | 6 | 11.6791 | 6.61139 | 10.9021 | 11.8288 | 1.85416 | 9.07135 | 10.0953 | 4.84001 | 9.81329 | 1.84273 | ...... | 1.92021 |
| 13 | 1156 | 12 | 11.6974 | 6.10076 | 11.1881 | 11.7902 | 2.16364 | 9.11673 | 9.62599 | 5.55435 | 10.0156 | 1.92944 | ...... | 2.53702 |
| 14 | 1156 | 24 | 11.6111 | 6.64487 | 11.2169 | 12.0325 | 2.27516 | 8.66302 | 9.56656 | 5.27267 | 10.1341 | 2.02315 | ...... | 2.99413 |
| 15 | 1156 | 72 | 11.6952 | 6.42792 | 11.357 | 12.1317 | 1.93882 | 8.75662 | 9.6897 | 5.1746 | 10.097 | 2.06766 | ...... | 2.56438 |
| 16 | 1164 | 2 | 10.914 | 6.49186 | 11.4692 | 12.2776 | 2.16589 | 7.47201 | 9.55829 | 5.42768 | 9.89126 | 2.1496 | ...... | 2.13586 |
| 17 | 1164 | 6 | 11.1104 | 6.33352 | 11.28 | 12.1229 | 2.32082 | 8.4694 | 9.53098 | 5.26888 | 9.71969 | 2.15781 | ...... | 2.54499 |
| 18 | 1164 | 12 | 11.0198 | 6.33934 | 11.5566 | 12.313 | 2.02921 | 7.83741 | 9.04214 | 5.0516 | 9.85302 | 1.94792 | ...... | 2.34146 |
| 19 | 1164 | 24 | 10.9839 | 6.43914 | 11.4892 | 12.3528 | 2.41837 | 7.41988 | 9.5853 | 5.48333 | 9.9366 | 2.13269 | ...... | 2.63246 |
| 20 | 1164 | 72 | 11.024 | 6.6182 | 11.5098 | 12.2709 | 1.98879 | 7.37891 | 9.44945 | 6.11647 | 9.84773 | 2.17367 | ...... | 2.42451 |
| Column Mean | | | 11.20 | 6.71 | 11.38 | 12.18 | 2.13 | 8.19 | 9.67 | 5.17 | 9.95 | 2.06 | ...... | 2.40 |
| Column Variance | | | 0.12 | 0.11 | 0.03 | 0.03 | 0.03 | 0.28 | 0.20 | 0.26 | 0.02 | 0.01 | ...... | 0.06 |
| Column Standard Dev. | | | 0.35 | 0.33 | 0.17 | 0.18 | 0.16 | 0.53 | 0.44 | 0.51 | 0.15 | 0.12 | ...... | 0.24 |

Figure 15

Standardized Centroid Matrix $Z=(x-m)/s$

| Observation | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| AADAC | -0.505 | -0.906 | -1.351 | -1.297 | -1.280 | 0.492 | 0.104 | 0.714 | -0.001 | -0.310 | 1.803 | 1.343 | 1.395 | 1.151 | 1.389 | -0.821 | -0.265 | -0.522 | -0.623 | -0.510 |
| ABAT | 1.477 | 1.258 | 1.509 | 1.621 | 1.269 | 0.295 | -0.269 | 0.309 | 0.270 | 0.129 | -0.780 | -0.288 | -1.822 | -0.188 | -0.840 | -0.648 | -1.123 | -1.106 | -0.806 | -0.268 |
| ABAT | 1.136 | 0.339 | 1.040 | -1.015 | 0.380 | 0.008 | -0.219 | 0.056 | 0.724 | 1.085 | -0.782 | -2.833 | -1.143 | -0.973 | -0.145 | 0.517 | -0.600 | 1.034 | 0.636 | 0.757 |
| ABAT | 0.091 | -0.091 | 0.728 | 0.407 | 0.105 | 0.285 | 1.040 | -0.325 | 0.511 | 1.631 | -1.693 | -1.935 | -2.148 | -0.808 | -0.259 | 0.548 | -0.308 | 0.744 | 0.964 | 0.511 |
| ABCA17P | -1.119 | 0.414 | 0.083 | -0.991 | 0.418 | 0.430 | 1.455 | 1.013 | -1.103 | -1.028 | 0.514 | -1.675 | 0.205 | 0.882 | -1.161 | 0.219 | 1.160 | -0.612 | 1.752 | -0.857 |
| ABCB1 | 0.151 | -0.631 | -0.690 | 0.300 | 0.064 | -0.383 | -0.673 | 0.364 | -0.307 | -0.513 | 1.470 | 1.657 | 1.743 | 0.887 | 1.064 | -1.360 | 0.522 | -0.671 | -1.458 | -1.536 |
| ABCB1 | 1.256 | 0.303 | -0.102 | 2.092 | 2.005 | -0.692 | -1.543 | -1.441 | -0.114 | 0.632 | -0.385 | 0.955 | -0.101 | -0.235 | 0.043 | -0.253 | -0.315 | -1.415 | -0.192 | -0.498 |
| ABCD3 | -0.120 | -0.211 | -1.755 | -2.051 | 0.364 | 0.029 | -0.448 | 1.136 | -0.351 | -1.430 | 1.636 | -0.656 | 0.749 | 0.195 | 0.002 | 0.500 | 0.188 | -0.240 | 0.609 | 1.854 |
| ABCD3 | -1.652 | -1.040 | 0.092 | -0.485 | -0.424 | 0.317 | 0.763 | 0.704 | 2.324 | 0.719 | 0.543 | -0.960 | 0.427 | 1.240 | 0.986 | -0.425 | -1.602 | -0.688 | -0.114 | -0.724 |
| ABHD1 | 0.901 | 0.454 | -0.022 | -0.143 | -0.645 | 0.912 | -0.352 | -1.612 | 0.597 | -0.831 | 2.059 | -1.924 | -1.170 | -0.355 | 0.032 | 0.744 | 0.815 | -1.010 | 0.597 | 0.953 |
| ... | | | | | | | | | | | | | | | | | | | | |
| ZNF423 | 0.597 | -0.249 | 0.661 | -1.314 | 0.652 | -0.512 | 0.335 | 0.290 | -1.311 | -0.574 | -0.555 | -1.983 | 0.558 | 2.441 | 0.671 | -1.095 | 0.591 | -0.248 | 0.951 | 0.094 |

Figure 16

Transpose Centroid $Z' = (x-m)'/s$

| Observation | Human | Time | AADAC | ABAT | ABAT | ABAT | ABCA17P | ABCB1 | ABCB1 | ABCD3 | ABCD3 | ABHD1 | ...... | ZNF423 |
|---|---|---|---|---|---|---|---|---|---|---|---|---|---|---|
| 1 | 1153 | 2 | -0.505 | 1.477 | 1.136 | 0.091 | -1.119 | 0.151 | 1.256 | -0.120 | -1.652 | 0.901 | ...... | 0.597 |
| 2 | 1153 | 6 | -0.906 | 1.258 | 0.339 | -0.091 | 0.414 | -0.631 | 0.303 | -0.211 | -1.040 | 0.454 | ...... | -0.249 |
| 3 | 1153 | 12 | -1.351 | 1.509 | 1.040 | 0.728 | 0.083 | -0.690 | -0.102 | -1.755 | 0.092 | -0.022 | ...... | 0.661 |
| 4 | 1153 | 24 | -1.297 | 1.621 | -1.015 | 0.407 | -0.991 | 0.300 | 2.092 | -2.051 | -0.485 | -0.143 | ...... | -1.314 |
| 5 | 1153 | 72 | -1.280 | 1.269 | 0.380 | 0.105 | 0.418 | 0.064 | 2.005 | 0.364 | -0.424 | -0.645 | ...... | 0.652 |
| 6 | 1154 | 2 | 0.492 | 0.295 | 0.008 | 0.285 | 0.430 | -0.383 | -0.692 | 0.029 | 0.317 | 0.912 | ...... | -0.512 |
| 7 | 1154 | 6 | 0.104 | -0.269 | -0.219 | 1.040 | 1.455 | -0.673 | -1.543 | -0.448 | 0.763 | -0.352 | ...... | 0.335 |
| 8 | 1154 | 12 | 0.714 | 0.309 | 0.056 | -0.325 | 1.013 | 0.364 | -1.441 | 1.136 | 0.704 | -1.612 | ...... | 0.290 |
| 9 | 1154 | 24 | -0.001 | 0.270 | 0.724 | 0.511 | -1.103 | -0.307 | -0.114 | -0.351 | 2.324 | 0.597 | ...... | -1.311 |
| 10 | 1154 | 72 | -0.310 | 0.129 | 1.085 | 1.631 | -1.028 | -0.513 | 0.632 | -1.430 | 0.719 | -0.831 | ...... | -0.574 |
| 11 | 1156 | 2 | 1.803 | -0.780 | -0.782 | -1.693 | 0.514 | 1.470 | -0.385 | 1.636 | 0.543 | 2.059 | ...... | -0.555 |
| 12 | 1156 | 6 | 1.343 | -0.288 | -2.833 | -1.935 | -1.675 | 1.657 | 0.955 | -0.656 | -0.960 | -1.924 | ...... | -1.983 |
| 13 | 1156 | 12 | 1.395 | -1.822 | -1.143 | -2.148 | 0.205 | 1.743 | -0.101 | 0.749 | 0.427 | -1.170 | ...... | 0.558 |
| 14 | 1156 | 24 | 1.151 | -0.188 | -0.973 | -0.808 | 0.882 | 0.887 | -0.235 | 0.195 | 1.240 | -0.355 | ...... | 2.441 |
| 15 | 1156 | 72 | 1.389 | -0.840 | -0.145 | -0.259 | -1.161 | 1.064 | 0.043 | 0.002 | 0.986 | 0.032 | ...... | 0.671 |
| 16 | 1164 | 2 | -0.821 | -0.648 | 0.517 | 0.548 | 0.219 | -1.360 | -0.253 | 0.500 | -0.425 | 0.744 | ...... | -1.095 |
| 17 | 1164 | 6 | -0.265 | -1.123 | -0.600 | -0.308 | 1.160 | 0.522 | -0.315 | 0.188 | -1.602 | 0.815 | ...... | 0.591 |
| 18 | 1164 | 12 | -0.522 | -1.106 | 1.034 | 0.744 | -0.612 | -0.671 | -1.415 | -0.240 | -0.688 | -1.010 | ...... | -0.248 |
| 19 | 1164 | 24 | -0.623 | -0.806 | 0.636 | 0.964 | 1.752 | -1.458 | -0.192 | 0.609 | -0.114 | 0.597 | ...... | 0.951 |
| 20 | 1164 | 72 | -0.510 | -0.268 | 0.757 | 0.511 | -0.857 | -1.536 | -0.498 | 1.854 | -0.724 | 0.953 | ...... | 0.094 |

Figure 17

| Mahalanobis Space | | | | | | | | | | | |
|---|---|---|---|---|---|---|---|---|---|---|---|
| Correlation Matrix -C for Normal Data | | | | | | | | | | | |
| | AADAC | ABAT | ABAT | ABAT | ABCA17P | ABCB1 | ABCB1 | ABCD3 | ABCD3 | ABHD1 | | ZNF423 |
| AADAC | 0.125 | -0.068 | -0.036 | -0.046 | -0.001 | 0.138 | -0.051 | 0.016 | 0.073 | 0.022 | ...... | 0.005 |
| ABAT | -0.068 | 0.111 | 0.015 | 0.020 | -0.011 | -0.039 | 0.081 | 0.019 | -0.085 | -0.008 | ...... | -0.008 |
| ABAT | -0.036 | 0.015 | 0.029 | 0.024 | 0.001 | -0.068 | -0.012 | -0.013 | -0.001 | 0.001 | ...... | 0.008 |
| ABAT | -0.046 | 0.020 | 0.024 | 0.033 | 0.001 | -0.082 | -0.007 | -0.034 | -0.034 | 0.001 | ...... | 0.000 |
| ABCA17P | -0.001 | -0.011 | 0.001 | 0.001 | 0.027 | -0.015 | -0.033 | 0.040 | 0.029 | 0.002 | ...... | 0.021 |
| ABCB1 | 0.138 | -0.039 | -0.068 | -0.082 | -0.015 | 0.281 | 0.052 | 0.101 | 0.013 | 0.009 | ...... | 0.003 |
| ABCB1 | -0.051 | 0.081 | -0.012 | -0.007 | -0.033 | 0.052 | 0.197 | -0.001 | -0.091 | -0.020 | ...... | -0.021 |
| ABCD3 | 0.016 | 0.019 | -0.013 | -0.034 | 0.040 | 0.101 | -0.001 | 0.245 | 0.033 | -0.009 | ...... | 0.046 |
| ABCD3 | 0.073 | -0.085 | -0.001 | -0.034 | 0.029 | 0.013 | -0.091 | 0.033 | 0.259 | 0.000 | ...... | 0.032 |
| ABHD1 | 0.022 | -0.008 | 0.001 | 0.001 | 0.002 | 0.009 | -0.020 | -0.009 | 0.000 | 0.021 | ...... | 0.003 |
| : | : | : | : | : | : | : | : | : | : | : | ...... | : |
| ZNF423 | 0.005 | -0.008 | 0.008 | 0.000 | 0.021 | 0.003 | -0.021 | 0.046 | 0.032 | 0.003 | ...... | 0.059 |
| Colum Mean | 11.20 | 6.71 | 11.38 | 12.18 | 2.13 | 8.19 | 9.67 | 5.17 | 9.95 | 2.06 | ........ | 2.40 |
| Col Std | 0.35 | 0.33 | 0.17 | 0.18 | 0.16 | 0.53 | 0.44 | 0.51 | 0.15 | 0.12 | ........ | 0.24 |
| Inverse Correlation Matrix -C^-1 for Normal Data | | | | | | | | | | | |
| | AADAC | ABAT | ABAT | ABAT | ABCA17P | ABCB1 | ABCB1 | ABCD3 | ABCD3 | ABHD1 | | ZNF423 |
| AADAC | 0.008 | -0.005 | 0.004 | -0.001 | -0.005 | 0.006 | -0.007 | 0.000 | 0.004 | 0.001 | ...... | 0.001 |
| ABAT | -0.005 | 0.018 | -0.005 | 0.003 | 0.003 | -0.003 | 0.006 | -0.009 | -0.013 | 0.001 | ...... | 0.005 |
| ABAT | 0.004 | -0.005 | 0.014 | 0.004 | -0.005 | -0.002 | -0.005 | -0.007 | 0.001 | 0.001 | ...... | 0.008 |
| ABAT | -0.001 | 0.003 | 0.004 | 0.006 | 0.004 | -0.008 | 0.002 | -0.012 | 0.000 | 0.000 | ...... | 0.009 |
| ABCA17P | -0.005 | 0.003 | -0.005 | 0.004 | 0.023 | -0.009 | 0.016 | -0.003 | 0.007 | 0.001 | ...... | 0.012 |
| ABCB1 | 0.006 | -0.003 | -0.002 | -0.008 | -0.009 | 0.038 | 0.009 | 0.032 | -0.017 | -0.006 | ...... | 0.002 |
| ABCB1 | -0.007 | 0.006 | -0.005 | 0.002 | 0.016 | 0.009 | 0.060 | 0.015 | -0.024 | -0.008 | ...... | 0.024 |
| ABCD3 | 0.000 | -0.009 | -0.007 | -0.012 | -0.003 | 0.032 | 0.015 | 0.057 | -0.021 | -0.005 | ...... | -0.015 |
| ABCD3 | 0.004 | -0.013 | 0.001 | 0.000 | 0.007 | -0.017 | -0.024 | -0.021 | 0.081 | 0.009 | ...... | -0.011 |
| ABHD1 | 0.001 | 0.001 | 0.001 | 0.000 | 0.001 | -0.006 | -0.008 | -0.005 | 0.009 | 0.005 | ...... | -0.006 |
| : | : | : | : | : | : | : | : | : | : | : | ...... | : |
| ZNF423 | 0.001 | 0.005 | 0.008 | 0.009 | 0.012 | 0.002 | 0.024 | -0.015 | -0.011 | -0.006 | ...... | 0.042 |

FIGURE 18

| Observation | Human | Time | µM | AADAC | ABAT | ABAT | ABAT | ABCA17P | ABCB1 | ABCB1 | ABCD3 | ABCD3 | ABHD1 | | ZNF423 |
|---|---|---|---|---|---|---|---|---|---|---|---|---|---|---|---|
| 1 | 1153 | 2 | 0.001 | 10.693 | 7.012 | 11.534 | 12.299 | 1.913 | 8.144 | 10.367 | 4.149 | 10.025 | 2.128 | ... | 2.185 |
| 2 | 1153 | 2 | 0.01 | 10.991 | 6.898 | 11.447 | 12.148 | 2.225 | 8.137 | 10.071 | 5.202 | 9.875 | 2.209 | ... | 2.505 |
| 3 | 1153 | 2 | 0.1 | 11.005 | 7.137 | 11.783 | 12.317 | 2.167 | 8.288 | 10.206 | 5.497 | 10.016 | 2.167 | ... | 2.133 |
| 4 | 1153 | 2 | 1 | 10.833 | 7.245 | 11.493 | 12.436 | 2.167 | 8.132 | 10.279 | 5.140 | 10.155 | 2.124 | ... | 2.199 |
| 5 | 1153 | 2 | 10 | 11.069 | 7.172 | 11.659 | 12.276 | 2.300 | 8.317 | 10.289 | 5.253 | 10.154 | 2.222 | ... | 2.393 |
| 6 | 1153 | 6 | 0.001 | 10.685 | 6.528 | 11.370 | 12.237 | 2.108 | 7.987 | 10.031 | 4.439 | 9.933 | 2.013 | ... | 1.963 |
| 7 | 1153 | 6 | 0.01 | 10.778 | 7.254 | 11.454 | 12.252 | 2.195 | 8.385 | 10.311 | 4.982 | 10.041 | 2.125 | ... | 2.160 |
| 8 | 1153 | 6 | 0.1 | 11.252 | 6.992 | 11.501 | 12.158 | 2.346 | 8.176 | 10.001 | 5.560 | 10.206 | 2.833 | ... | 2.504 |
| 9 | 1153 | 6 | 1 | 11.469 | 6.857 | 11.453 | 12.061 | 2.162 | 8.336 | 10.239 | 5.758 | 10.544 | 2.221 | ... | 2.628 |
| 10 | 1153 | 6 | 10 | 11.387 | 6.868 | 11.462 | 12.205 | 2.039 | 8.679 | 10.614 | 5.931 | 10.655 | 1.861 | ... | 1.939 |
| 11 | 1153 | 12 | 0.001 | 10.659 | 7.400 | 11.550 | 12.449 | 2.262 | 8.190 | 10.147 | 4.515 | 9.877 | 1.883 | ... | 2.309 |
| 12 | 1153 | 12 | 0.01 | 11.011 | 7.037 | 11.681 | 12.257 | 2.281 | 8.134 | 10.268 | 4.476 | 10.114 | 2.143 | ... | 2.403 |
| 13 | 1153 | 12 | 0.1 | 11.192 | 6.947 | 11.317 | 12.187 | 2.231 | 8.047 | 10.620 | 4.999 | 10.480 | 2.024 | ... | 2.608 |
| 14 | 1153 | 12 | 1 | 11.657 | 6.791 | 10.964 | 12.032 | 1.994 | 8.223 | 10.978 | 5.645 | 10.624 | 1.889 | ... | 2.080 |
| 15 | 1153 | 12 | 10 | 11.653 | 6.970 | 11.375 | 12.057 | 2.395 | 8.375 | 11.082 | 5.709 | 10.802 | 2.617 | ... | 2.179 |
| 16 | 1153 | 24 | 0.001 | 10.787 | 7.131 | 11.573 | 12.153 | 2.023 | 8.284 | 10.675 | 4.916 | 9.884 | 2.354 | ... | 2.230 |
| 17 | 1153 | 24 | 0.01 | 10.919 | 7.178 | 11.525 | 12.273 | 1.936 | 8.254 | 11.013 | 4.700 | 10.051 | 1.953 | ... | 2.124 |
| 18 | 1153 | 24 | 0.1 | 11.307 | 6.965 | 11.439 | 12.288 | 2.030 | 8.568 | 11.496 | 4.201 | 10.102 | 1.884 | ... | 2.085 |
| 19 | 1153 | 24 | 1 | 11.718 | 6.819 | 11.345 | 11.946 | 2.155 | 8.587 | 11.670 | 5.704 | 10.456 | 2.296 | ... | 2.552 |
| : | : | : | : | : | : | : | : | : | : | : | : | : | : | : | : |
| 100 | 1164 | 72 | 10 | 12.020 | 5.760 | 11.209 | 11.977 | 2.783 | 7.910 | 11.309 | 6.460 | 10.699 | 2.316 | ... | 3.791 |

FIGURE 19

| Observation | 1 | 2 | 3 | 4 | 5 | 6 | 7 | 8 | 9 | 10 | 11 | 12 | 13 | 14 | 15 | 16 | 17 | 18 | 19 | ... | 100 |
|---|---|---|---|---|---|---|---|---|---|---|---|---|---|---|---|---|---|---|---|---|---|
| AADAC | -1.247 | -0.497 | -0.463 | -0.896 | -0.303 | -1.267 | -1.034 | 0.160 | 0.704 | 0.497 | -1.334 | -0.447 | 0.008 | 1.177 | 1.168 | -1.011 | -0.680 | 0.297 | 1.330 | ... | 2.092 |
| ABAT | 0.178 | -0.137 | 0.526 | 0.827 | 0.622 | -1.163 | 0.851 | 0.123 | -0.250 | -0.220 | 1.255 | 0.250 | 0.000 | -0.434 | 0.063 | 0.509 | 0.639 | 0.050 | -0.357 | ... | -3.290 |
| ABAT | 0.439 | -0.032 | 1.790 | 0.215 | 1.116 | -0.447 | 0.005 | 0.258 | -0.001 | 0.047 | 0.524 | 1.239 | -0.735 | -2.651 | -0.422 | 0.651 | 0.392 | -0.073 | -0.584 | ... | -1.324 |
| ABAT | 0.710 | -0.349 | 0.838 | 1.677 | 0.551 | 0.272 | 0.383 | -0.282 | -0.963 | 0.051 | 1.767 | 0.414 | -0.075 | -1.169 | -0.988 | -0.314 | 0.527 | 0.631 | -1.769 | ... | -1.551 |
| ABCA17P | -1.480 | 0.138 | -0.164 | -0.164 | 0.528 | -0.470 | -0.017 | 0.766 | -0.188 | -0.827 | 0.329 | 0.427 | 0.170 | -1.061 | 1.017 | -0.911 | -1.358 | -0.875 | -0.227 | ... | 3.028 |
| ABCB1 | -0.625 | -0.657 | 0.085 | -0.684 | 0.228 | -1.397 | 0.563 | -0.464 | 0.321 | 2.007 | -0.397 | -0.671 | -1.102 | -0.233 | 0.513 | 0.066 | -0.085 | 1.463 | 1.556 | ... | -1.773 |
| ABCB1 | -0.496 | -1.067 | -0.808 | -0.666 | -0.647 | -1.144 | -0.604 | -1.203 | -0.742 | -0.018 | -0.921 | -0.687 | -0.007 | 0.685 | 0.884 | 0.099 | 0.751 | 1.684 | 2.020 | ... | 1.323 |
| ABCD3 | -1.745 | -0.022 | 0.460 | -0.124 | 0.061 | -1.271 | -0.383 | 0.563 | 0.888 | 1.169 | -1.147 | -1.211 | -0.355 | 0.702 | 0.807 | -0.490 | -0.843 | -1.660 | 0.799 | ... | 2.035 |
| ABCD3 | -0.797 | -1.293 | -0.825 | -0.369 | -0.370 | -1.100 | -0.744 | -0.200 | 0.917 | 1.284 | -1.286 | -0.504 | 0.705 | 1.181 | 1.768 | -1.262 | -0.711 | -0.542 | 0.627 | ... | 1.429 |
| ABHD1 | -0.133 | 0.180 | 0.018 | -0.148 | 0.228 | -0.573 | -0.144 | 2.576 | 0.226 | -1.158 | -1.074 | -0.075 | -0.533 | -1.052 | 1.748 | 0.736 | -0.805 | -1.071 | 0.513 | ... | 0.589 |
| ... | ... | ... | ... | ... | ... | ... | ... | ... | ... | ... | ... | ... | ... | ... | ... | ... | ... | ... | ... | ... | ... |
| ZNF423 | -0.392 | 0.374 | -0.519 | -0.360 | 0.107 | -0.927 | -0.453 | 0.373 | 0.669 | -0.984 | -0.095 | 0.131 | 0.623 | -0.646 | -0.408 | -0.284 | -0.539 | -0.634 | 0.486 | ... | 3.459 |

FIGURE 20

| Observation | Human | Time | µM | AADAC | ABAT | ABAT | ABAT | ABCA17 | ABCB1 | ABCB1 | ABCD3 | ABCD3 | ABHD1 | ABHD1 | ZNF423 |
|---|---|---|---|---|---|---|---|---|---|---|---|---|---|---|---|
| 1 | 1153 | 2 | 0.001 | -1.247 | 0.178 | 0.439 | 0.710 | -1.480 | -0.625 | -0.496 | -1.745 | -0.797 | -0.133 | ...... | -0.392 |
| 2 | 1153 | 2 | 0.01 | -0.497 | -0.137 | -0.032 | -0.349 | 0.138 | -0.657 | -1.067 | -0.022 | -1.293 | 0.180 | ...... | 0.374 |
| 3 | 1153 | 2 | 0.1 | -0.463 | 0.526 | 1.790 | 0.838 | -0.164 | 0.085 | -0.808 | 0.460 | -0.825 | 0.018 | ...... | -0.519 |
| 4 | 1153 | 2 | 1 | -0.896 | 0.827 | 0.215 | 1.677 | -0.164 | -0.684 | -0.666 | -0.124 | -0.369 | -0.148 | ...... | -0.360 |
| 5 | 1153 | 2 | 10 | -0.303 | 0.622 | 1.116 | 0.551 | 0.528 | 0.228 | -0.647 | 0.061 | -0.370 | 0.228 | ...... | 0.107 |
| 6 | 1153 | 6 | 0.001 | -1.267 | -1.163 | -0.447 | 0.272 | -0.470 | -1.397 | -1.144 | -1.271 | -1.100 | -0.573 | ...... | -0.927 |
| 7 | 1153 | 6 | 0.01 | -1.034 | 0.851 | 0.005 | 0.383 | -0.017 | 0.563 | -0.604 | -0.383 | -0.744 | -0.144 | ...... | -0.453 |
| 8 | 1153 | 6 | 0.1 | 0.160 | 0.123 | 0.258 | -0.282 | 0.766 | -0.464 | -1.203 | 0.563 | -0.200 | 2.576 | ...... | 0.373 |
| 9 | 1153 | 6 | 1 | 0.704 | -0.250 | -0.001 | -0.963 | -0.188 | 0.321 | -0.742 | 0.888 | 0.917 | 0.226 | ...... | 0.669 |
| 10 | 1153 | 6 | 10 | 0.497 | -0.220 | 0.047 | 0.051 | -0.827 | 2.007 | -0.018 | 1.169 | 1.284 | -1.158 | ...... | -0.984 |
| 11 | 1153 | 12 | 0.001 | -1.334 | 1.255 | 0.524 | 1.767 | 0.329 | -0.397 | -0.921 | -1.147 | -1.286 | -1.074 | ...... | -0.095 |
| 12 | 1153 | 12 | 0.01 | -0.447 | 0.250 | 1.239 | 0.414 | 0.427 | -0.671 | -0.687 | -1.211 | -0.504 | -0.075 | ...... | 0.131 |
| 13 | 1153 | 12 | 0.1 | 0.008 | 0.000 | -0.735 | -0.075 | 0.170 | -1.102 | -0.007 | -0.355 | 0.705 | -0.533 | ...... | 0.623 |
| 14 | 1153 | 12 | 1 | 1.177 | -0.434 | -2.651 | -1.169 | -1.061 | -0.233 | 0.685 | 0.702 | 1.181 | -1.052 | ...... | -0.646 |
| 15 | 1153 | 12 | 10 | 1.168 | 0.063 | -0.422 | -0.988 | 1.017 | 0.513 | 0.884 | 0.807 | 1.768 | 1.748 | ...... | -0.408 |
| 16 | 1153 | 24 | 0.001 | -1.011 | 0.509 | 0.651 | -0.314 | -0.911 | 0.066 | 0.099 | -0.490 | -1.262 | 0.736 | ...... | -0.284 |
| 17 | 1153 | 24 | 0.01 | -0.680 | 0.639 | 0.392 | 0.527 | -1.358 | -0.085 | 0.751 | -0.843 | -0.711 | -0.805 | ...... | -0.539 |
| 18 | 1153 | 24 | 0.1 | 0.297 | 0.050 | -0.073 | 0.631 | -0.875 | 1.463 | 1.684 | -1.660 | -0.542 | -1.071 | ...... | -0.634 |
| 19 | 1153 | 24 | 1 | 1.330 | -0.357 | -0.584 | -1.769 | -0.227 | 1.556 | 2.020 | 0.799 | 0.627 | 0.513 | ...... | 0.486 |
| ... | ... | ... | ... | ... | ... | ... | ... | ... | ... | ... | ... | ... | ... | ... | ... |
| 100 | 1164 | 72 | 10 | 2.092 | -3.290 | -1.324 | -1.551 | 3.028 | -1.773 | 1.323 | 2.035 | 1.429 | 0.589 | ...... | 3.459 |

FIGURE 21

| Human - 1153 | 1153 | 1153 | 1153 | 1153 | 1153 | 1153 | 1153 | 1153 | 1153 | 1153 | 1153 | 1153 | 1153 |
|---|---|---|---|---|---|---|---|---|---|---|---|---|---|
| Time - Hours | 2 | 2 | 2 | 2 | 2 | 6 | 6 | 6 | 6 | 6 | 12 | 12 | 12 |
| Concentration - µM | 0.001 | 0.01 | 0.1 | 1 | 10 | 0.001 | 0.01 | 0.1 | 1 | 10 | 0.001 | 0.01 | 0.1 |
| MD | 20.30 | 12.16 | 18.21 | 32.02 | 39.19 | 23.19 | 12.75 | 28.65 | 59.57 | 70.62 | 10.81 | 11.33 | 40.59 |

| Human - 1153 | 1153 | 1153 | 1153 | 1153 | 1153 | 1153 | 1153 | 1153 | 1153 | 1153 | 1153 | 1153 |
|---|---|---|---|---|---|---|---|---|---|---|---|---|
| Time - Hours | 12 | 12 | 24 | 24 | 24 | 24 | 24 | 72 | 72 | 72 | 72 | 72 |
| Concentration - µM | 1 | 10 | 0.001 | 0.01 | 0.1 | 1 | 10 | 0.001 | 0.01 | 0.1 | 1 | 10 |
| MD | 80.15 | 108.28 | 6.01 | 8.27 | 29.42 | 87.83 | 103.33 | 8.34 | 13.30 | 63.62 | 106.61 | 142.30 |

| Human - 1154 | 1154 | 1154 | 1154 | 1154 | 1154 | 1154 | 1154 | 1154 | 1154 | 1154 | 1154 | 1154 | 1154 |
|---|---|---|---|---|---|---|---|---|---|---|---|---|---|
| Time - Hours | 2 | 2 | 2 | 2 | 2 | 6 | 6 | 6 | 6 | 6 | 12 | 12 | 12 |
| Concentration - µM | 0.001 | 0.01 | 0.1 | 1 | 10 | 0.001 | 0.01 | 0.1 | 1 | 10 | 0.001 | 0.01 | 0.1 |
| MD | 17.13 | 14.92 | 19.21 | 30.16 | 35.07 | 10.14 | 15.08 | 29.28 | 92.07 | 110.55 | 17.77 | 10.42 | 32.98 |

| Human - 1154 | 1154 | 1154 | 1154 | 1154 | 1154 | 1154 | 1154 | 1154 | 1154 | 1154 | 1154 | 1154 |
|---|---|---|---|---|---|---|---|---|---|---|---|---|
| Time - Hours | 12 | 12 | 24 | 24 | 24 | 24 | 24 | 72 | 72 | 72 | 72 | 72 |
| Concentration - µM | 1 | 10 | 0.001 | 0.01 | 0.1 | 1 | 10 | 0.001 | 0.01 | 0.1 | 1 | 10 |
| MD | 60.21 | 82.03 | 8.47 | 9.65 | 36.53 | 81.76 | 136.58 | 8.57 | 30.69 | 88.37 | 146.56 | 179.27 |

| Human - 1156 | 1156 | 1156 | 1156 | 1156 | 1156 | 1156 | 1156 | 1156 | 1156 | 1156 | 1156 | 1156 | 1156 |
|---|---|---|---|---|---|---|---|---|---|---|---|---|---|
| Time - Hours | 2 | 2 | 2 | 2 | 2 | 6 | 6 | 6 | 6 | 6 | 12 | 12 | 12 |
| Concentration - µM | 0.001 | 0.01 | 0.1 | 1 | 10 | 0.001 | 0.01 | 0.1 | 1 | 10 | 0.001 | 0.01 | 0.1 |
| MD | 23.56 | 15.87 | 13.43 | 27.09 | 30.20 | 20.61 | 20.45 | 23.36 | 37.43 | 55.09 | 12.70 | 20.20 | 24.46 |

| Human - 1156 | 1156 | 1156 | 1156 | 1156 | 1156 | 1156 | 1156 | 1156 | 1156 | 1156 | 1156 | 1156 |
|---|---|---|---|---|---|---|---|---|---|---|---|---|
| Time - Hours | 12 | 12 | 24 | 24 | 24 | 24 | 24 | 72 | 72 | 72 | 72 | 72 |
| Concentration - µM | 1 | 10 | 0.001 | 0.01 | 0.1 | 1 | 10 | 0.001 | 0.01 | 0.1 | 1 | 10 |
| MD | 54.07 | 83.64 | 10.00 | 8.02 | 34.55 | 66.90 | 116.84 | 10.25 | 18.13 | 49.03 | 78.18 | 113.25 |

| Human - 1164 | 1164 | 1164 | 1164 | 1164 | 1164 | 1164 | 1164 | 1164 | 1164 | 1164 | 1164 | 1164 | 1164 |
|---|---|---|---|---|---|---|---|---|---|---|---|---|---|
| Time - Hours | 2 | 2 | 2 | 2 | 2 | 6 | 6 | 6 | 6 | 6 | 12 | 12 | 12 |
| Concentration - µM | 0.001 | 0.01 | 0.1 | 1 | 10 | 0.001 | 0.01 | 0.1 | 1 | 10 | 0.001 | 0.01 | 0.1 |
| MD | 16.69 | 12.78 | 12.89 | 27.10 | 37.07 | 19.47 | 15.40 | 27.44 | 54.07 | 57.09 | 43.33 | 15.75 | 46.68 |

| Human - 1164 | 1164 | 1164 | 1164 | 1164 | 1164 | 1164 | 1164 | 1164 | 1164 | 1164 | 1164 | 1164 |
|---|---|---|---|---|---|---|---|---|---|---|---|---|
| Time - Hours | 12 | 12 | 24 | 24 | 24 | 24 | 24 | 72 | 72 | 72 | 72 | 72 |
| Concentration - µM | 1 | 10 | 0.001 | 0.01 | 0.1 | 1 | 10 | 0.001 | 0.01 | 0.1 | 1 | 10 |
| MD | 95.35 | 102.29 | 21.32 | 12.06 | 56.63 | 104.21 | 127.06 | 11.76 | 30.10 | 65.10 | 115.32 | 172.20 |

FIGURE 22

| Time - Hours | 2 | 2 | 2 | 2 | 2 | 2 | 6 | 6 | 6 | 6 | 6 | 6 | 12 | 12 | 12 |
|---|---|---|---|---|---|---|---|---|---|---|---|---|---|---|---|
| Concentration - µM | 0.001 | 0.01 | 0.1 | 1 | 10 | 0.001 | 0.01 | 0.1 | 1 | 10 | 0.001 | 0.01 | 0.1 |
| Average MD | 19.42 | 13.93 | 15.94 | 29.09 | 35.38 | 18.35 | 15.92 | 27.18 | 60.78 | 73.34 | 21.15 | 14.42 | 36.18 |
| P-value | 0.454 | 0.018 | 0.283 | 0.003 | 0.003 | 0.922 | 0.281 | 0.006 | 0.033 | 0.023 | 0.708 | 0.206 | 0.033 |

| Time - Hours | 12 | 12 | 24 | 24 | 24 | 24 | 24 | 72 | 72 | 72 | 72 | 72 |
|---|---|---|---|---|---|---|---|---|---|---|---|---|
| Concentration - µM | 1 | 10 | 0.001 | 0.01 | 0.1 | 1 | 10 | 0.001 | 0.01 | 0.1 | 1 | 10 |
| Average MD | 72.44 | 94.06 | 11.45 | 9.50 | 39.28 | 85.18 | 120.95 | 9.73 | 23.06 | 66.53 | 111.67 | 151.76 |
| P-value | 0.010 | 0.001 | 0.147 | 0.003 | 0.038 | 0.003 | 0.001 | 0.002 | 0.334 | 0.009 | 0.007 | 0.003 |

FIGURE 23

| Ob. | ACOX1 | ACOX1 | ACOX1 | ACOX1 | ACOX1 | ANGPTL4 | ANGPTL4 | APOA2 | APOA2 | APOA4 | ...... | SLC25A20 |
|---|---|---|---|---|---|---|---|---|---|---|---|---|
| 1 | 3.09 | -0.63 | 0.23 | -0.82 | -1.15 | -1.50 | -1.70 | 0.00 | 0.25 | -0.61 | ...... | -1.55 |
| 2 | -0.17 | -1.12 | -0.01 | -0.85 | -0.78 | -1.16 | -1.20 | -0.14 | 0.34 | -0.46 | ...... | -0.93 |
| 3 | 0.13 | -1.38 | -0.11 | -0.94 | -1.11 | -0.93 | -0.75 | 0.00 | -0.08 | -0.78 | ...... | -0.86 |
| 4 | -0.31 | 0.31 | 0.52 | 0.08 | -0.54 | 0.30 | 0.38 | -0.26 | -0.36 | 0.23 | ...... | -0.72 |
| 5 | -1.28 | -0.98 | 0.10 | -0.67 | -0.31 | 0.57 | 0.32 | -0.38 | -0.15 | -0.54 | ...... | -0.21 |
| 6 | 0.87 | -1.06 | -0.48 | -1.87 | -0.98 | -1.85 | -1.77 | -1.05 | -0.85 | -0.71 | ...... | -1.52 |
| 7 | 1.32 | -0.65 | -1.38 | -0.98 | -0.93 | -1.26 | -1.25 | -0.82 | -1.00 | -0.77 | ...... | -1.31 |
| 8 | -0.62 | -0.31 | -0.71 | -0.01 | -0.16 | -0.08 | 0.28 | -1.06 | -0.71 | -0.74 | ...... | 0.12 |
| 9 | -1.04 | 0.03 | -2.00 | 0.24 | 0.80 | 0.93 | 1.05 | -0.44 | -0.23 | -0.77 | ...... | 1.05 |
| 10 | -0.67 | 0.55 | 0.54 | 0.60 | 0.60 | 1.03 | 1.01 | -0.21 | 0.05 | -0.26 | ...... | 1.05 |
| 11 | -0.34 | -0.94 | -0.89 | -1.00 | -1.50 | -0.70 | -0.49 | -0.68 | -0.84 | -0.58 | ...... | -0.97 |
| 12 | -0.99 | -1.17 | 0.02 | -0.99 | -0.54 | -0.52 | -0.70 | -0.47 | -0.64 | -0.93 | ...... | -0.32 |
| 13 | 0.35 | 0.86 | 0.39 | 0.79 | 0.38 | 0.86 | 0.59 | -0.16 | -0.64 | 0.06 | ...... | 0.56 |
| 14 | 2.73 | 1.22 | 1.81 | 0.93 | 1.12 | 1.07 | 0.94 | -0.33 | -0.33 | -0.06 | ...... | 1.25 |
| 15 | -0.76 | 1.31 | 0.34 | 1.48 | 1.36 | 1.40 | 1.53 | 0.45 | 0.35 | 0.42 | ...... | 1.73 |
| 16 | 0.85 | -1.42 | 0.92 | -1.28 | -1.03 | -1.07 | -1.13 | -0.28 | -0.20 | -0.76 | ...... | -0.89 |
| 17 | 0.30 | 0.38 | -1.24 | 0.54 | -0.71 | -1.24 | -1.49 | 0.41 | 0.18 | 0.31 | ...... | -0.87 |
| 18 | 0.18 | 1.38 | -0.24 | 1.19 | 0.55 | -0.20 | -0.21 | 1.06 | 0.87 | 1.75 | ...... | -0.05 |
| 19 | .. | .. | .. | .. | .. | .. | .. | .. | .. | .. | ...... | .. |
| 100 | -0.86 | 0.73 | 0.98 | 0.85 | 1.93 | 1.01 | 0.98 | 3.19 | 3.17 | 2.28 | ...... | 1.18 |

FIGURE 24

| Time | µM | MD Mean | P Value |
|---|---|---|---|
| 2 | 0.001 | 248.90 | 0.676 |
| 2 | 0.01 | 163.83 | 0.560 |
| 2 | 0.1 | 105.00 | 0.025 |
| 2 | 1 | 180.70 | 0.379 |
| 2 | 10 | 227.55 | 0.955 |
| 6 | 0.001 | 172.83 | 0.379 |
| 6 | 0.01 | 212.76 | 0.920 |
| 6 | 0.1 | 501.25 | 0.243 |
| 6 | 1 | 1011.43 | 0.036 |
| 6 | 10 | 1361.90 | 0.051 |
| 12 | 0.001 | 211.25 | 0.871 |
| 12 | 0.01 | 161.13 | 0.440 |
| 12 | 0.1 | 611.88 | 0.324 |
| 12 | 1 | 940.38 | 0.044 |
| 12 | 10 | 1012.63 | 0.013 |

| Time | µM | MD Mean | P Value |
|---|---|---|---|
| 24 | 0.001 | 154.83 | 0.560 |
| 24 | 0.01 | 143.38 | 0.359 |
| 24 | 0.1 | 415.50 | 0.023 |
| 24 | 1 | 973.98 | 0.003 |
| 24 | 10 | 1235.80 | 0.002 |
| 72 | 0.001 | 112.38 | 0.109 |
| 72 | 0.01 | 397.85 | 0.386 |
| 72 | 0.1 | 972.28 | 0.029 |
| 72 | 1 | 1300.03 | 0.009 |
| 72 | 10 | 1461.40 | 0.007 |

FIGURE 25

| α = .05 | 0.001 µM | 0.01 µM | 0.1 µM | 1 µM | 10 µM |
|---|---|---|---|---|---|
| 2 hrs | 19.42 | 13.93 | 15.95 | 29.09 | 35.38 |
| P-value | 0.454 | 0.018 | 0.283 | 0.003 | 0.003 |
| 6 hrs | 18.35 | 15.92 | 27.18 | 60.78 | 73.34 |
| P-value | 0.922 | 0.601 | 0.006 | 0.033 | 0.023 |
| 12 hrs | 21.15 | 14.42 | 36.17 | 72.44 | 94.06 |
| P-value | 0.708 | 0.206 | 0.033 | 0.01 | 0.001 |
| 24 hrs | 11.45 | 9.5 | 39.28 | 85.18 | 120.95 |
| P-value | 0.147 | 0.003 | 0.036 | 0.003 | 0.001 |
| 72 hrs | 9.73 | 23.06 | 66.53 | 111.67 | 151.76 |
| P-value | 0.002 | 0.334 | 0.009 | 0.007 | 0.003 |

FIGURE 26

| α = .05 | 2 hrs | 6 hrs | 12 hrs | 24 hrs | 72 hrs |
|---|---|---|---|---|---|
| 0.001 µM | 19.42 | 18.35 | 21.15 | 11.45 | 9.73 |
| P-value | 0.454 | 0.922 | 0.708 | 0.147 | 0.002 |
| 0.01 µM | 13.93 | 15.92 | 14.42 | 9.5 | 23.06 |
| P-value | 0.018 | 0.601 | 0.206 | 0.003 | 0.334 |
| 0.1 µM | 15.95 | 27.18 | 36.17 | 39.28 | 66.53 |
| P-value | 0.283 | 0.006 | 0.033 | 0.036 | 0.009 |
| 1 µM | 29.09 | 60.78 | 72.44 | 85.18 | 111.67 |
| P-value | 0.003 | 0.033 | 0.01 | 0.003 | 0.007 |
| 10 µM | 35.38 | 73.34 | 94.06 | 120.95 | 151.76 |
| P-value | 0.003 | 0.023 | 0.001 | 0.001 | 0.003 |

FIGURE 27

| µM / Hours | 2 | 6 | 12 | 24 | 72 |
|---|---|---|---|---|---|
| .001 | .454/19.42 | .922/18.35 | .708/21.15 | .147/11.45 | .002/9.73 |
| .01 | .018/13.93 | .281/15.92 | .206/14.42 | .003/9.5 | .334/23.06 |
| .1 | .283/15.95 | .006/27.18 | .033/36.17 | .036/39.28 | .009/66.53 |
| 1 | .003/29.09 | .033/60.78 | .01/72.44 | .003/85.18 | .007/111.67 |
| 10 | .003/35.38 | .023/73.34 | .001/94.06 | .001/120.95 | .003/151.76 |

FIGURE 28

| µM / Hours | 2 | 6 | 12 | 24 | 72 |
|---|---|---|---|---|---|
| .001 | (14.34, 24.50) | (9.30, 27.41) | (-2.83, 45.14) | (0.66, 22.24) | (7.19, 12.27) |
| .01 | (11.15, 16.72) | (10.76, 21.08) | (7.27, 21.58) | (6.55, 12.45) | (9.20, 36.91) |
| .1 | (10.78, 21.09) | (22.95, 31.42) | (20.88, 51.48) | (20.27, 58.29) | (40.65, 92.42) |
| 1 | (25.23, 32.96) | (24.37, 97.20) | (43.15, 100.74) | (60.61, 109.74) | (66.87, 156.47) |
| 10 | (29.27, 41.50) | (32.36, 114.31) | (73.05, 115.07) | (98.28, 143.62) | (103.60, 199.91) |

METHODS AND SYSTEMS FOR HIGH-THROUGHPUT TOXICITY SCREENING OF A COMPOUND USING MAHALANOBIS VALUES

CROSS-REFERENCE TO RELATED APPLICATIONS

Provided per USPTO rules by Application Data Sheet.

STATEMENT REGARDING FEDERALLY SPONSORED R&D

Provided per USPTO rules by Application Data Sheet.

NAMES OF PARTIES TO JOINT RESEARCH AGREEMENT

Provided per USPTO rules by Application Data Sheet.

REFERENCE TO SEQUENCE LISTING

Provided per USPTO rules by Application Data Sheet.

STATEMENT RE PRIOR DISCLOSURES

Provided per USPTO rules by Application Data Sheet.

BACKGROUND

Field of the Invention

The invention relates to methods and systems for high-throughput toxicity screening of compounds using Mahalanobis Values, and in particular comparing a normal unexposed transcriptome Mahalanobis Value in an in-vitro hepatocyte microassay against a calculated transcriptome Mahalanobis Value of hepatocytes exposed to a target compound for varying time periods and in varying concentrations.

Description of the Related Art

Currently, there are well over 80,000 pre-existing, commercially available chemical compounds in use in the United States that have never been tested for toxicity risk levels. This number continues to increase by approximately 2,000 per year. The European Union estimates that they need to evaluate a similar number of substances as well. When these compounds are exposed to humans, they could cause some type of human health hazard (National Research Council, 2007).

Traditional testing methods have relied on numerous laboratory animals for a single compound which is expensive and very time-consuming (Bouhifd et al., 2015). To conduct a thorough risk assessment of these chemicals it will require approximately 54 million vertebrate animals and cost approximately $10 billion over the next 10 years using traditional toxicity testing methods (Hartung & Rovida, 2009). There must be a revolution in toxicity testing methods in order to adequately evaluate each chemical in a timely manner. An alternative and new approach in applying systems engineering tools and analysis to determine toxicogenomics risk levels from hazardous compound exposure could revolutionize toxicity testing and bring it into the $21^{st}$ century.

In early 2000, the Environmental Protection Agency (EPA) requested that the National Research Council (NRC) review current scientific methods to develop a new vision and strategy for toxicity testing in the $21^{st}$ century. The state of science has since evolved significantly to offer alternatives to animal based toxicity testing. New tools and methods have been at the forefront to bring in a new era of toxicity testing by leveraging system engineering tools, systems biology tools, computational toxicology and advances in toxicogenomics, and bioinformatics. These new methods move away from animal based models to introduce in-vitro based methods that could evaluate human cell lines more cost effectively and efficiently.

Animal based approaches remain very expensive when compared to in-vitro methods (Humane Society International,) and extrapolation of animal based test results for human risk assessment often lead to different physiological outcomes (National Research Council, 2007). By leveraging systems engineering tools and analysis it could move the science away from slow apical-endpoint testing to rapid dose and time response testing to reduce delays. This would provide valuable information to decision-makers and scientists in evaluating the potential risk of new and existing chemicals to human health in an efficient and timely manner, and therefore reduce risk (National Research Council, 2007). In 2012 the National Research Defense Council reiterated the recommendations from the NRC to strengthen toxic chemical risk assessments especially in the areas of dose-response, risk characterization, hazardous assessment, and determining the level of exposure (Janssen, Sass, Schettler, & Solomon, 2012). Accordingly, there remains a need to provide methods and systems for performing toxic chemical risk assessments.

BRIEF SUMMARY OF THE INVENTION

Accordingly, to address the existing problems and issues in the prior art, there is provided a method for displaying toxicity of a chemical, comprising the steps: (i) Performing a transcriptome array analysis of a hepatocyte cell line exposed to the chemical, wherein the hepatocyte cell line is exposed to at least five different concentrations of the chemical ranging from 0.001-10 micromolar to form at least five concentration samples of the hepatocyte cell line, and each concentration sample of the five different concentration samples are exposed to the chemical for at least five different time periods ranging from 2-72 hours to form at least 25 concentration-duration samples of the hepatocyte cell line; (ii) Calculating an Abnormal Mahalanobis Distance Value and a Abnormal p-value for each concentration-duration sample of the at least 25 concentration-duration samples of the hepatocyte cell line; (iii) Calculating an Mahalanobis Distance number for 1-risk deviation, 2-risk deviations, and 3-risk deviations from a Normal Mahalanobis Distance, where the Normal Mahalanobis Distance is calculated from a transcriptome array analysis of a hepatocyte cell line unexposed to the chemical; (iv) Visually presenting the Abnormal Mahalanobis Distance Values on a grid of chemical concentrations against times of exposure, where the chemical concentrations are the at least five different concentrations of the chemical ranging from 0.001-10 micromolar and the times of exposure are the at least five different time periods ranging from 2-72 hours; and, (v) Visually marking the grid of Abnormal Mahalanobis Distance Values to identify the 1-risk deviation, 2-risk deviations, and 3-risk deviations from Normal Mahalanobis Distance, wherein the marking of the 1-risk deviation, 2-risk deviations, and 3-risk deviations displays toxicity of a chemical over the range of concentrations and exposure time periods.

In one preferred embodiment, the method specifies wherein the at least five different concentrations of the chemical ranging from 0.001-10 micromolar comprise 0.001, 0.01, 0.1, 1.0, and 10.0 micromolar.

In another preferred embodiment, the method specifies where the at least five different time periods ranging from 2-72 hours comprise 2, 6, 12, 24, and 72 hours.

In another preferred embodiment, there is provided a method for high-throughput toxicity screening of a compound, comprising the steps: (i) Administering a compound to human hepatocytes in an in-vitro microassay having a plurality of sample wells; (ii) Exposing the hepatocytes to the compound for at least two or more different time periods and at two or more different concentrations; (iii) Forming a selection of a baseline of unstressed normal cells using a selection of the hepatocytes having an exposure time of 0 and a concentration of 0; (iv) Forming a selection of a baseline of stressed abnormal cells using a selection of hepatocytes having an exposure time greater than 0 and a concentration of greater than zero; (v) Obtaining transcriptomics data from the baseline of normal cells and the baseline of abnormal cells by identifying statistically significant up-regulated or down-regulated genes in the hepatocytes using two or more RNA-ligand probes; (vi) Calculating a Normal Mahalanobis Value using transcriptomics data from the baseline of normal cells using Equation 1, $MD_j = D_j^2 = Z'_{ij} C^{-1} Z_{ij}$, and Equation 2 $Z_{ij} = (X_{ij} - m_i)/s_i$; where $X_{ij}$=value of the $i^{th}$ characteristic (gene) of the $j^{th}$ observation (experiment); $m_i$=mean of the $i^{th}$ characteristic (gene); $s_i$=standard deviation of the $i^{th}$ characteristic (gene); $Z_{ij} = (z_{1j}, z_{2j}, z_{3j}, \ldots z_{kj})$ standardized vector of the standardized values of the $X_{ij}$; $Z_{ij}'$=transpose of the $Z_{ij}$ standardized vector; $C^{-1}$=inverse of the correlation matrix; k=total number of gene measurements (n variables); (vii) Calculating an Abnormal Mahalanobis Value using transcriptomics data from the baseline of abnormal cells using Equation 1 and Equation 2; and (viii) Calculating a Toxicity Risk Ratio by dividing the Normal Mahalanobis Value by the Abnormal Mahalanobis Value.

In another preferred embodiment, there is provided a method as described and claimed wherein the hepatocytes comprise two or more samples of hepatocytes, each sample obtained at a different time or from a different location than the other.

In another preferred embodiment, there is provided a method as described and claimed wherein the hepatocytes comprise at least four samples of hepatocytes, each sample obtained at a different time or from a different location than the other.

In another preferred embodiment, there is provided a method as described and claimed wherein the step of exposing the hepatocytes to the compound for at least two or more different time periods comprises exposing the hepatocytes to the compound for five time periods defined as 2, 6, 12, 24, and 72 hours.

In another preferred embodiment, there is provided a method as described and claimed wherein the step of exposing the hepatocytes to the compound at two or more different concentrations comprises exposing the hepatocytes to the compound at six different concentrations defined as 0.0, 0.001, 0.01, 0.1, 1.0, 10.0 micro Molar.

In another preferred embodiment, there is provided a method as described and claimed wherein the step of obtaining transcriptomics data from the baseline of normal cells and the baseline of abnormal cells by identifying statistically significant up-regulated or down-regulated genes in the hepatocytes using two or more RNA-ligand probes comprises using at least five RNA-ligand probes.

In another preferred embodiment, there is provided a system for high-throughput toxicity screening of a chemical, comprising: (i) a transcriptomics Micro Array Chip with affixed Probes; (ii) a Micro Array Chip Scanner; (iii) a Micro Array Chip Fluidics Station; (iv) a Micro Array Chip Hybridization Oven; and (v) a System software, wherein the system software comprises computer program instructions readable on a processor for: (a) performing transcriptomics steps of extracting mRNA from a hepatocyte cell line exposed to the chemical, wherein the hepatocyte cell line is exposed to at least five different concentrations of the chemical ranging from 0.001-10 micromolar to form at least five concentration samples of the hepatocyte cell line, and each concentration sample of the five different concentration samples are exposed to the chemical for at least five different time periods ranging from 2-72 hours to form at least 25 concentration-duration samples of the hepatocyte cell line; (b) reverse transcribing the mRNA to cDNA; (c) transcribing the cDNA to biotin-labelled cRNA; (d) fragmenting the biotin-labelled cRNA; (e) hybridizing the fragmented biotin-labelled cRNA to the transcriptomics Micro Array Chip; (f) Washing and Staining the Hybridized MicroArray; and (g) Scanning and Quantitating the Scan Results; and (vi) a Mahalanobis Distance software module operatively associated with the system software wherein the Mahalanobis Distance software module comprises computer program instructions readable on a processor for performing Mahalanobis Distance analysis, and Displaying a 3-derivation Grid of toxicity of the chemical over the range of concentrations and exposure time periods.

In another preferred embodiment, there is provided a system for high-throughput toxicity screening of a compound, comprising: (i) human hepatocytes in an in-vitro microassay having a plurality of sample wells; (ii) an RNA-ligand kit comprising two or more RNA-ligands, and sufficient reagents, buffers, capture agents, detection complexes, instructions, enzymes or polymerases, nucleic acids or fragments, and containers for obtaining transcriptomics data from the baseline of normal cells and the baseline of abnormal cells by identifying statistically significant up-regulated or down-regulated genes in the hepatocytes using two or more RNA-ligand probes; and (iii) means for quantifying up-regulation or down-regulation of genes in hepatocytes.

BRIEF DESCRIPTION OF THE SEVERAL VIEWS OF DRAWING

Figure 8:
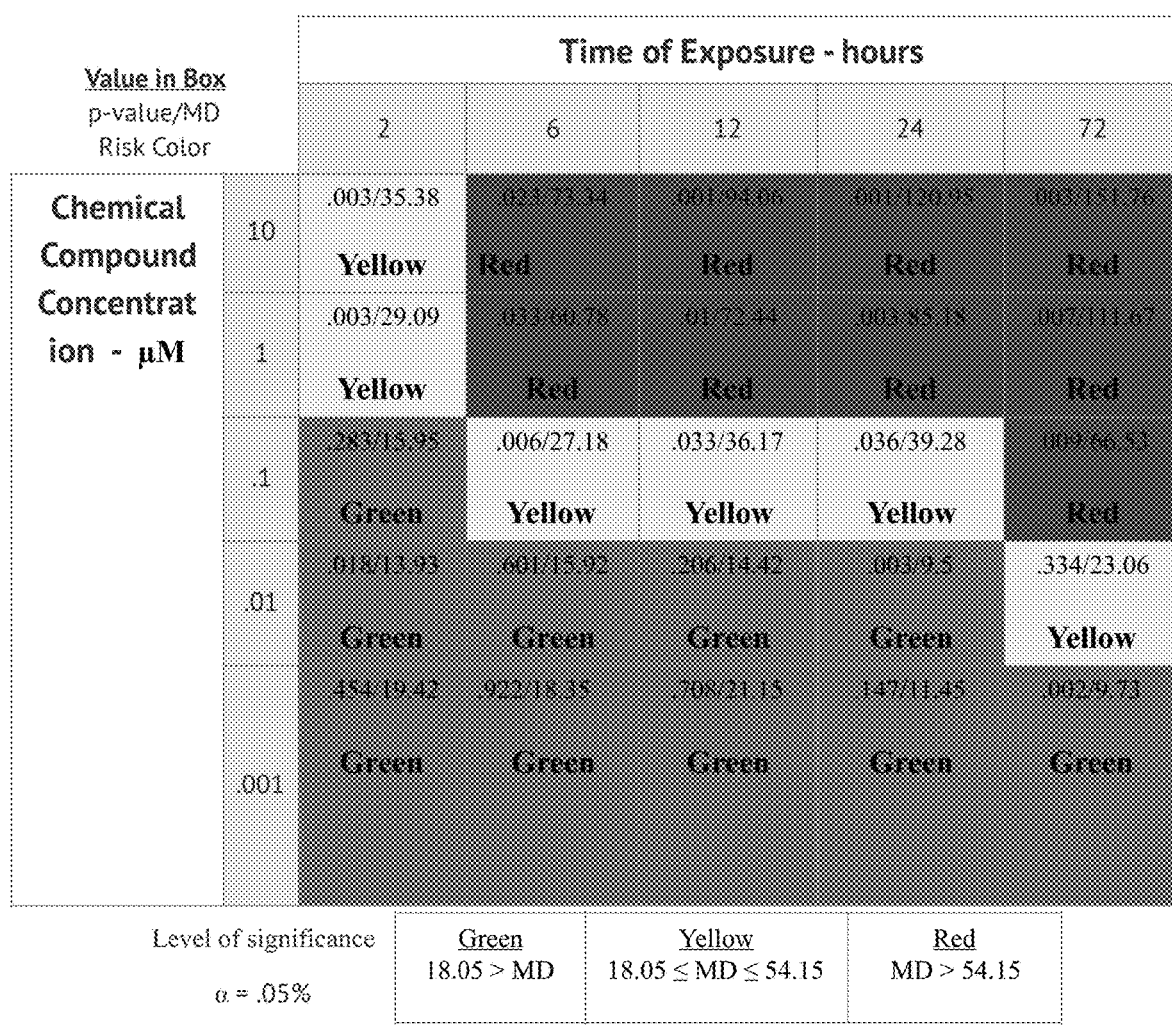

FIG. 8 is a grid diagram and illustrates (i) a visual presentation of the Abnormal Mahalanobis Distance Values on a grid of chemical concentrations against times of exposure, where the chemical concentrations are the at least five different concentrations of the chemical ranging from 0.001-10 micromolar and the times of exposure are the at least five different time periods ranging from 2-72 hours; and, (ii) a visual marking of the grid of Abnormal Mahalanobis Distance Values to identify the 1-risk deviation, 2-risk deviations, and 3-risk deviations from Normal Mahalanobis Distance, wherein the marking of the 1-risk deviation, 2-risk deviations, and 3-risk deviations displays toxicity of a chemical over the range of concentrations and exposure time periods.

Figure 9:
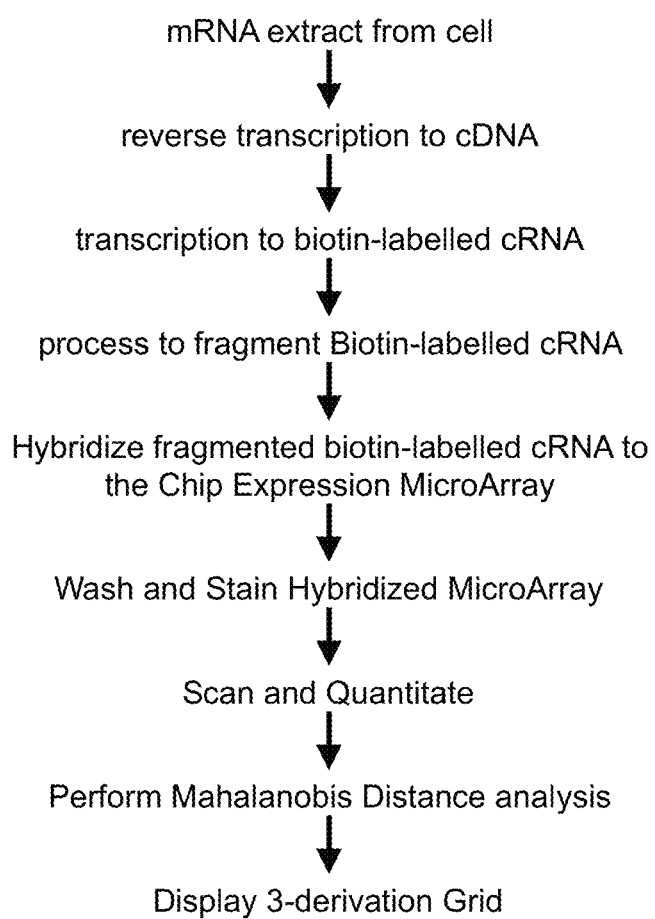

FIG. 9 is a flow diagram and illustrates steps in a Micro Array Transcriptomics Chip System that includes a Mahalanomics Distance module and visual toxicity display according to the present invention.

Figure 10:
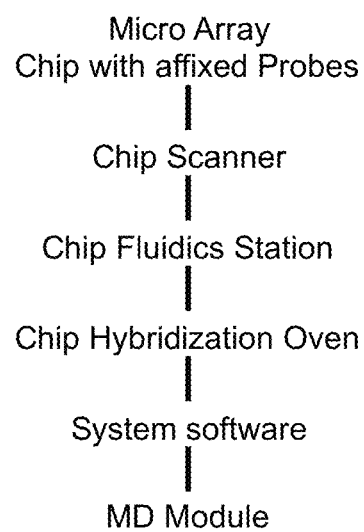

FIG. 10 is a flow diagram and illustrates components in a Micro Array Transcriptomics Chip System that includes a Mahalanomics Distance module and visual toxicity display according to the present invention.

Figure 11:
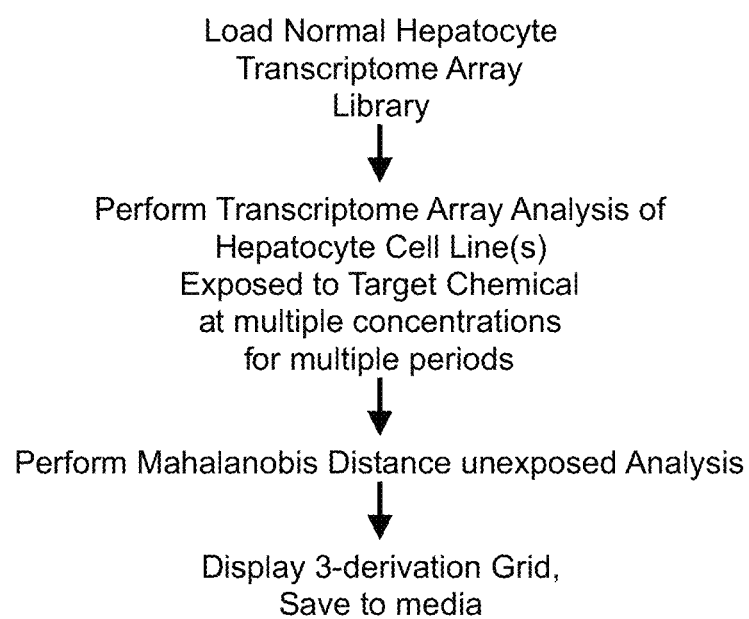

FIG. 11 is a flow diagram and illustrates a transcriptomics system pre-loaded with a hepatocyte library for faster comparison against a hepatocyte sample that is exposed to a target chemical compound for toxicity analysis and display.

FIG. 12 is a chart illustrating comparative features of different models for testing chemical toxicity.

Figure 13:
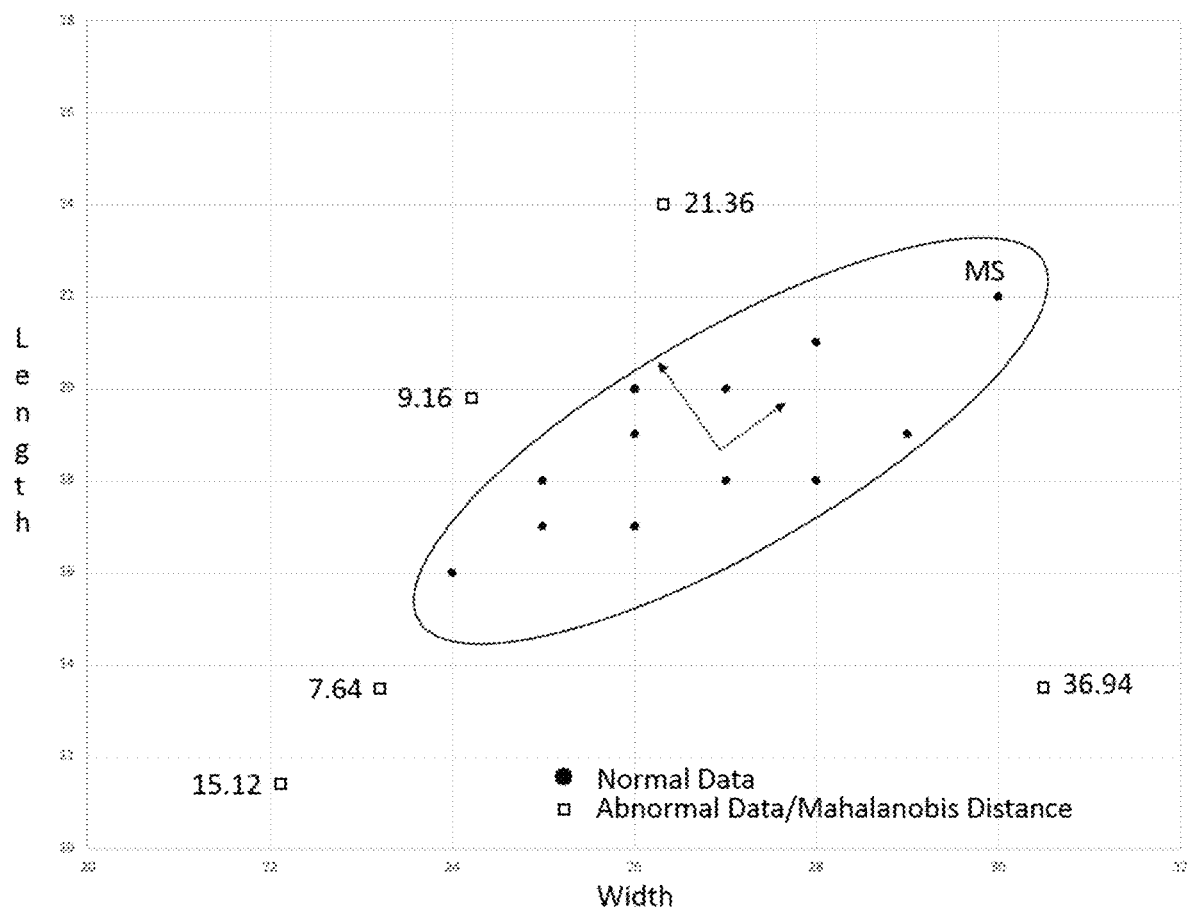

FIG. 13 is a graph illustrating a two-dimensional plot of Normal Data in a Mahalanobis Space and shows Mahalanobis Distance for Abnormal Data.

FIG. 14 is an illustration of a snapshot of the database of Normal Unexposed Observation Data.

FIG. 15 is an illustration of a snapshot of the database showing a centroid-standardized matrix.

FIG. 16 is an illustration of a snapshot of the database showing transposing the centroid matrix of FIG. 15 in order to conduct a matrix operation.

FIG. 17 is an illustration of a snapshot of the database showing the Mahalanobis Space (MS)(Normal) and the mean, standard deviation, and correlation matrix along with the inverse correlation matrix that describes the structure and internal relationships of the genes in the normal group.

FIG. 18 is an illustration of a snapshot of the database showing (perturbed) the abnormal group as calculated.

FIG. 19 is an illustration of a snapshot of the database showing a centroid dataset of the abnormal group.

FIG. 20 is an illustration of a snapshot of the database showing that a centroid matrix for the abnormal dataset is transposed.

FIG. 21 is a chart and shows the MD results for human cell lines 1153, 1154, 1156, 1164.

FIG. 22 is a chart and shows mean MDs from the four different human cell lines (1153, 1154, 1156, 1164) for each of the perturbed experiments (varying time and concentration) and the results.

FIG. 23 is an illustration of a snapshot of a database of a reduced sample set that probed only 10 genes across four cell lines across five time periods—2, 6, 12, 24, 72 hours—and five concentrations—0.001, 0.01, 0.1, 1.0, and 10.0 micromolar concentration.

FIG. 24 is a chart and shows mean MDs from the four different human cell lines (1153, 1154, 1156, 1164) for each of the perturbed experiments (varying time and concentration).

FIG. 25 is a chart and shows the MD number and p-value at a level of significance of 0.05 for the different concentration levels of exposure from GW7647 versus the different exposure times.

FIG. 26 is a chart and shows the exposure time versus the concentration level.

FIG. 27 is a chart and shows a summary of the p-values for the MD number at the different times and concentration levels.

FIG. 28 is a chart and shows a 95% confidence interval for each perturbation.

DETAILED DESCRIPTION OF THE INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Systems engineering tools and analysis is an approach and framework that can be used to solve very complex system-of-systems problems from mechanical systems to biological systems. A system that is simple and easily understood for example is a desktop computer composed of numerous systems that when combined are a system-of-systems platform. The liver is composed of a system-of-systems and the tools and analysis techniques from systems engineering can be applied to hepatocytes as well. A hepatocyte cell (liver cell) in a human body is composed of numerous systems and these include the lysosome, cytoplasm, nuclear membrane, vacuole, mitochondrion, ribosomes, nucleus, nucleolus, golgi, endoplasmic reticulum, centriole, peroxisome, and cell membrane. These systems make up one cell and are very complex and not completely understood. The cell interacts with numerous hepatocytes to create a network of systems that interact with other human cells. This highly complex network of systems is responsible for responding to foreign and hazardous compounds that enter the human body. Some of these compounds will be metabolized and processed by human hepatocytes. As these liver cells metabolize and process foreign compounds, the hepatocyte may recover or become highly stressed and mutate. This state of high stress can result in a malfunction in the transcription of RNA in the human liver cells during reproduction and eventually develop into cancer.

Transcriptomic Technologies

Transcriptomics describes the global measurement of mRNA transcripts in a biologic system. This collection of mRNA transcripts represents the transcription of all genes at a point in time. Technologies that allow the simultaneous analysis of thousands of transcripts have made it possible to analyze transcriptomes.

Technologic Approaches

Technologies for assaying gene, protein, and metabolic expression profiles are not new inventions. Measurements of gene expression have evolved from the single measures of steady-state mRNA using Northern blot analysis to the more global analysis of thousands of genes using DNA microarrays and serial analysis of gene expression (SAGE), the two dominant technologies. The advantage of global approaches is the ability of a single investigation to query the behavior of hundreds, thousands, or tens of thousands of biologic molecules in a single assay. For example, in profiling gene expression, one might use technologies such as Northern blot analysis to look at expression of a single gene, but Northern Blot has low throughput. Quantitative real-time reverse transcriptase PCR (qRT-PCR), often used with subtractive cloning or differential display, can easily be used to study the expression of 10 or more genes, but these are either not always comprehensive or follow up full-length cloning is required.

Techniques such as SAGE allow the entire collection of transcripts to be catalogued without assumptions about what is actually expressed (unlike microarrays, where one needs to select probes from a catalogue of genes). SAGE is a technology based on sequencing strings of short expressed sequence tags representing both the identity and the frequency of occurrence of specific sequences within the transcriptome. However, SAGE is costly and relatively low throughput, because each sample to be analyzed requires a SAGE Tag library to be constructed and sequenced. Massively parallel signature sequencing speeds up the SAGE process with a bead-based approach that simultaneously sequences multiple tags, but it is costly.

DNA microarray technology can be used to generate large amounts of data at moderate cost but is limited to surveys of genes that are included in the microarray. In this technology, a solid matrix surface supports thousands of different, surface-bound DNAs, which are hybridized against a pool of RNA to measure gene expression. A systematic comparison indicates that gene expression measured by oligonucleotide microarrays correlates well with SAGE in transcriptional profiling, particularly for genes expressed at high levels (Kim 2003).

DNA Microarray Technology

As used herein, microarray technology enables the simultaneous analysis of all transcripts in a system. DNA microarrays contain collections of oligonucleotide sequences located in precise locations in a high-density format. Two complementary DNA (cDNA) microarray formats have come to dominate the field. Spotted microarrays are prepared from synthesized cDNAs or oligonucleotide probes that are printed on a treated glass slide surface in a high-density format. These spotted arrays were the first widely used DNA microarrays (Schena et al. 1995, 1996) and were originally printed in individual investigators' laboratories from collections of clones. Complications in characterizing, managing, and standardizing these collections led to substantial variability in performance. Commercially produced oligonucleotide microarrays, in which oligonucleotides are synthesized in situ using inkjet printing, have largely replaced cDNA microarrays (Hughes et al. 2001). Whole-genome microarrays for human and mouse genomes contain 40,000-45,000 features corresponding to unique genes and transcripts. The probes range from 20 to 60 bp and individual microarrays typically contain between 5,000 and 50,000 features. The longer probes provide improved sensitivity and tolerance of polymorphic sequence mismatches. Several commercial vendors provide spotted arrays or variants of this technology and development in this area continues (Hardiman 2004).

The alternative technology uses photolithographic synthesis of oligonucleotide probes on a quartz surface and was developed by Affymetrix (Fodor et al. 1993; Pease et al. 1994; Lipshutz et al. 1999). These GeneChip arrays are characterized by very high probe densities (up to 1.3 million probes per chip) and typically consist of up to 25-mer probes (probes with 25-base residues). Each "gene" may be represented by as many as 20 overlapping probe sequences and paired mismatch probes, which contain sequence substitutions that enable quantitative evaluation of nonspecific hybridization. Elaboration of this mismatch strategy also allows analysis of SNPs by microarray analysis (see SNP discussion in section above). Considerable research into probe design has contributed to the improvement of microarray performance and has facilitated the standardization of transcriptome analysis.

Other array formats have been developed. Nylon membranes and plastic microarrays have been used with varying degrees of success (Qian et al. 2005). Nylon membranes produce low- to medium-density cDNA microarrays, whereas plastic retains the advantages of glass for producing high-density microarrays that are somewhat cheaper than glass slide arrays. The probes for nylon arrays are typically labeled with radioactive phosphorus isotopes (32P or 33P) to afford increases in sensitivity, but this approach is not favored because of problems associated with the use of radioactivity and efficiency of analysis.

Affymetrix and other major commercial vendors (Agilent, GE Healthcare [formerly Amersham], and Applied Biosystems) currently offer several different microarrays corresponding to essentially all known genes and transcripts for human as well as similar microarray products for model organisms used in toxicity studies. In addition, Affymetrix also offers whole-genome microarrays for application to SNP mapping and detection (see above).

Experimental Details of Transcriptome Profiling with Microarrays

Figure 1:
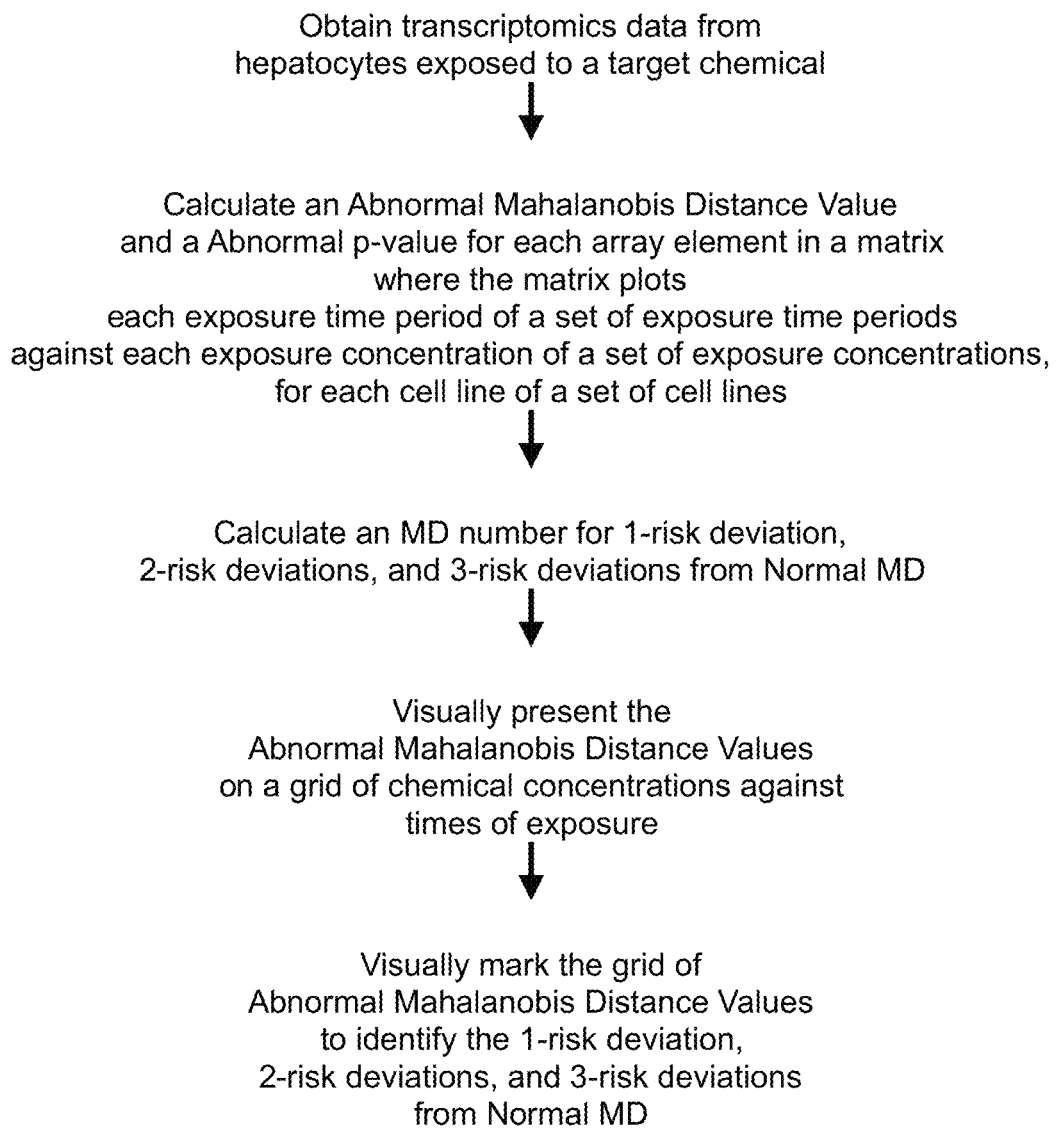
FIG. 1 is a flow diagram illustrating a five-part embodiment of the invention illustrating multiple exposure concentrations and multiple exposure durations.
Figure 2:
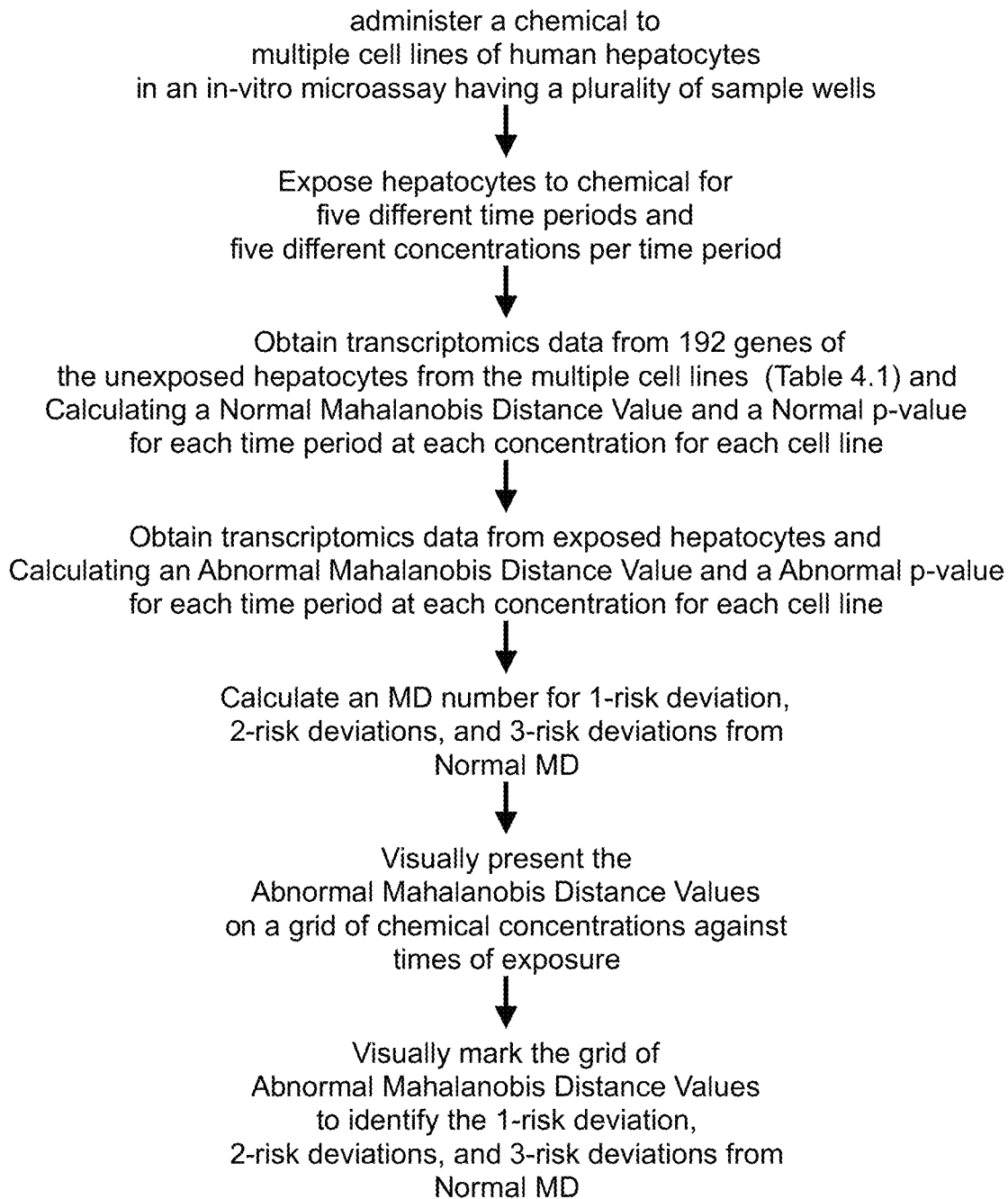
FIG. 2 is a flow diagram illustrating a seven-part embodiment of the invention using a smaller transcriptomics data set, e.g. a 192-gene subset, for fast processing.
Figure 3:
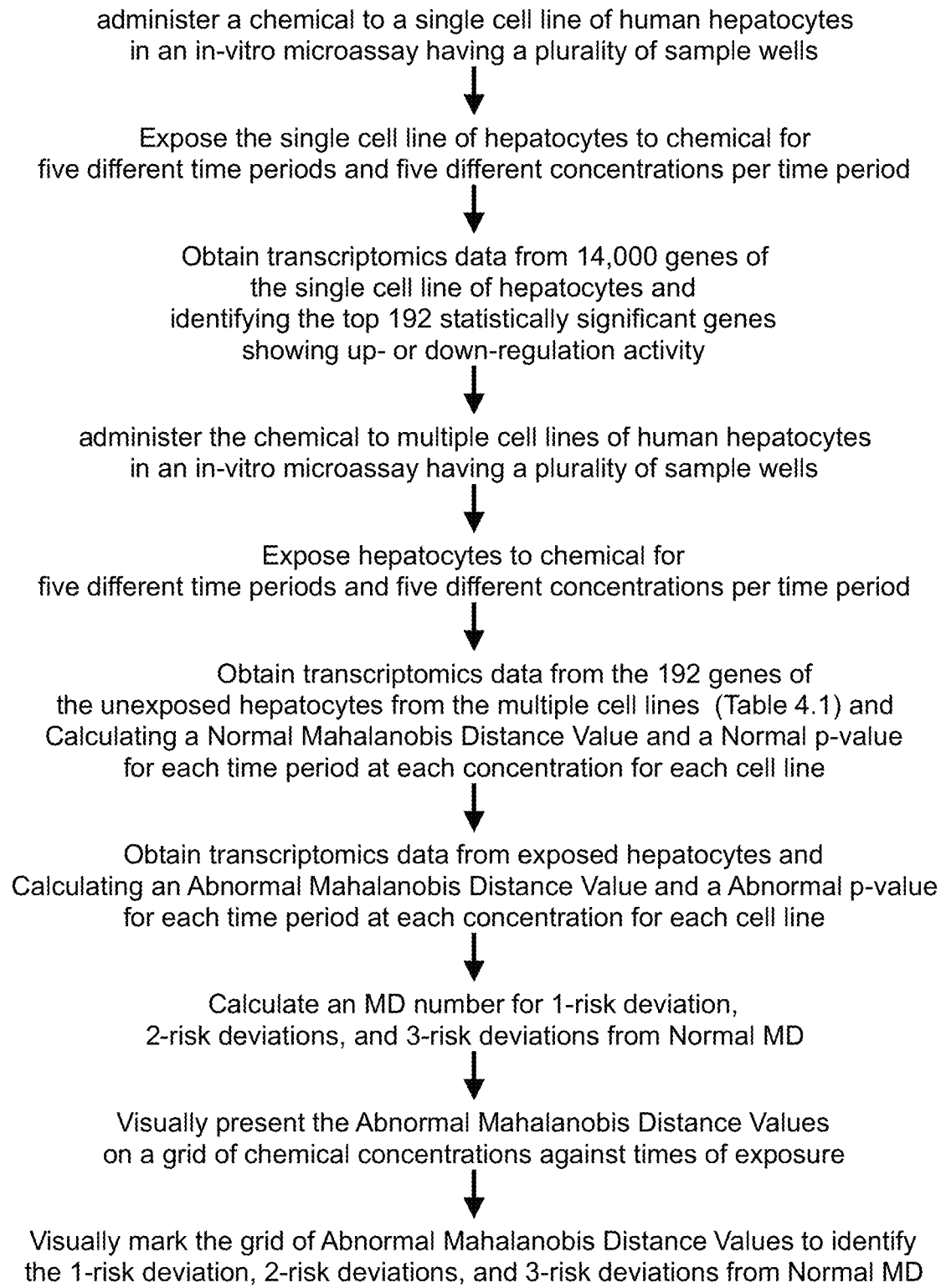
FIG. 3 is a flow diagram illustrating a ten-part embodiment of the invention using a pre-scan of a large transcriptomics data set to identify a smaller transcriptomics data set to speed processing of multiple cell line samples.
Figure 4:
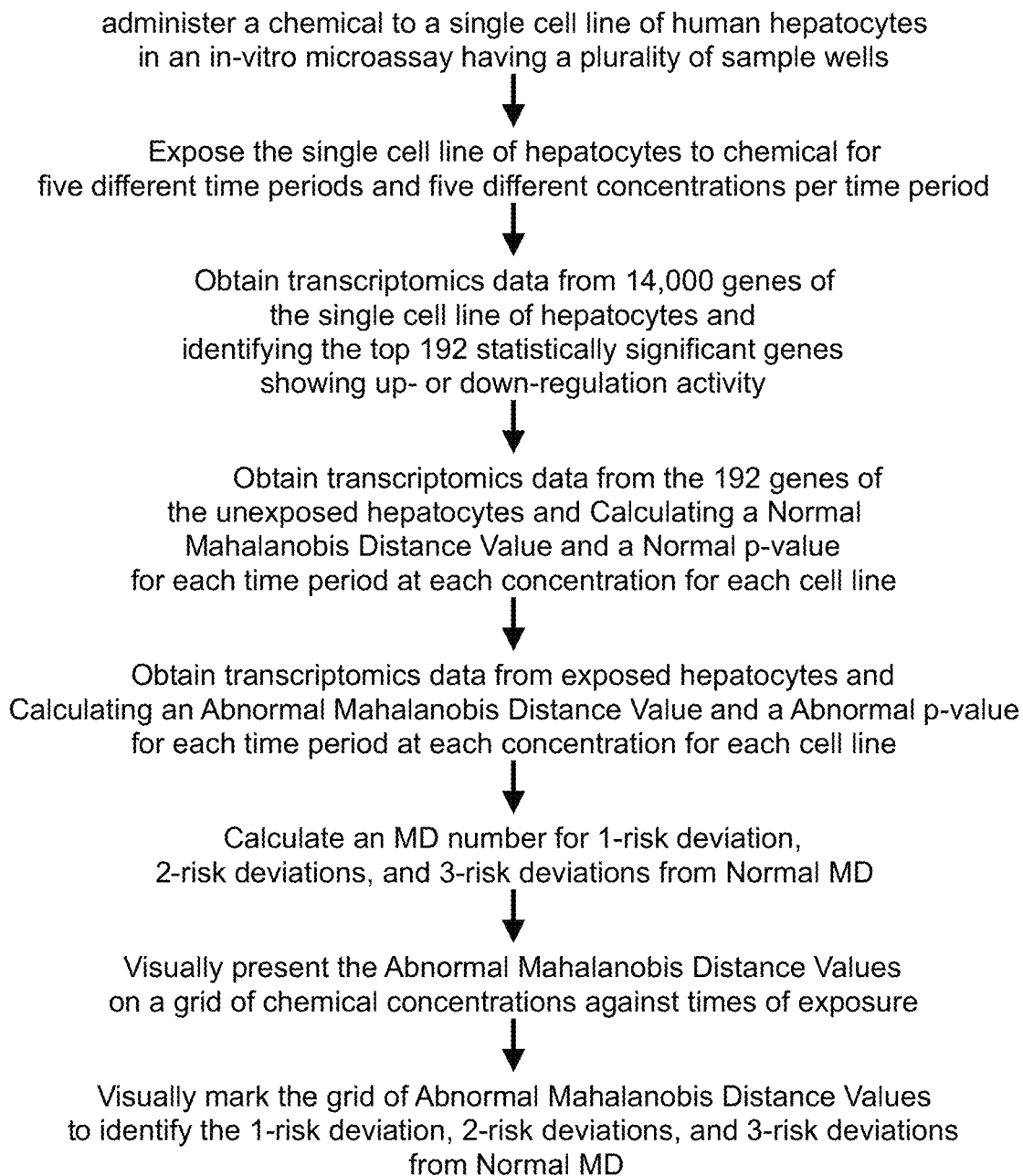
FIG. 4 is a flow diagram illustrating a eight-part embodiment of the invention for a single cell line using a pre-scan of a large transcriptomics data set, e.g. 14 k, to identify a smaller transcriptomics data set, e.g. 192, to speed processing of a single cell line sample.
Figure 5:
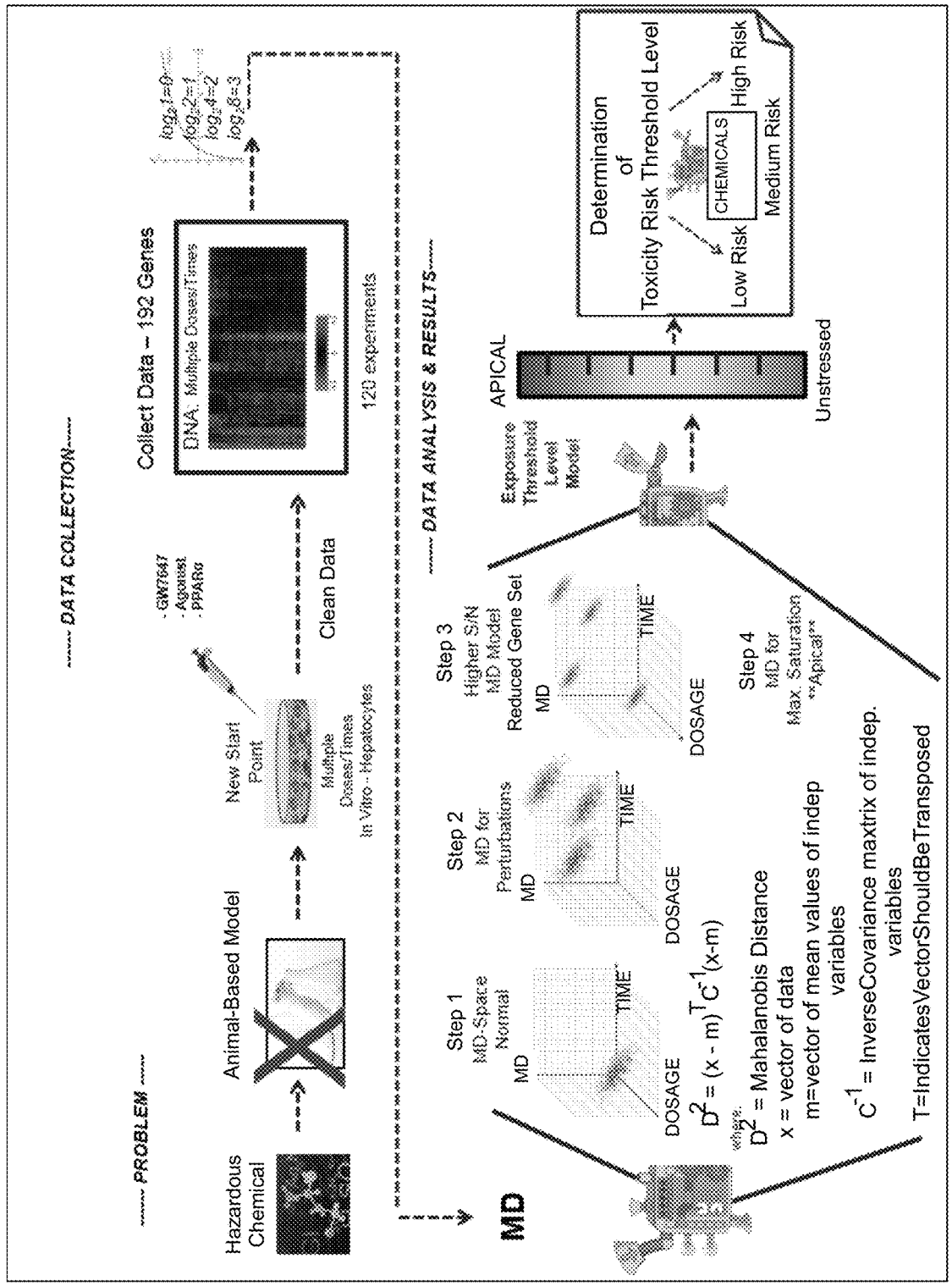
FIG. 5 is a flow diagram illustrating a system according to the present invention used for evaluating toxicity of a chemical compound that is metabolised by liver cells.
Figure 6:
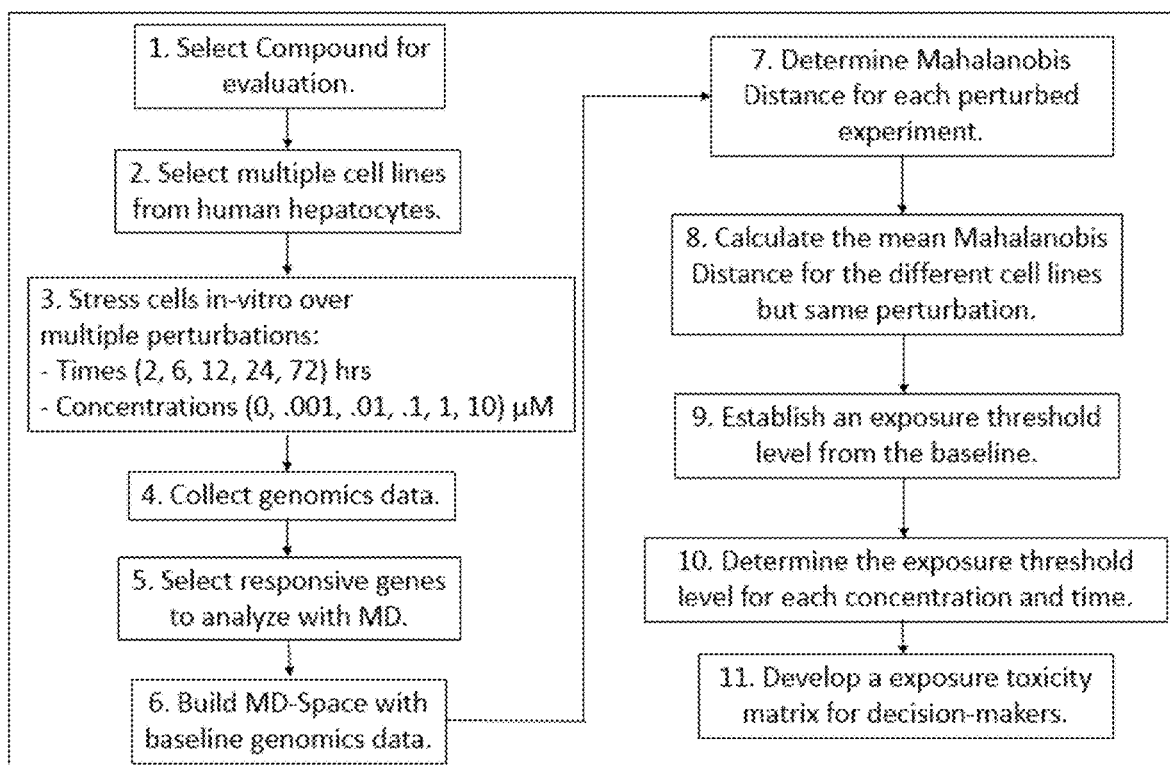
FIG. 6 is a flow diagram illustrating a hepatocyte toxicogenomics evaluation process and shows the flow from the selection of human liver cell lines to the establishment of the risk threshold scale.
Figure 7:
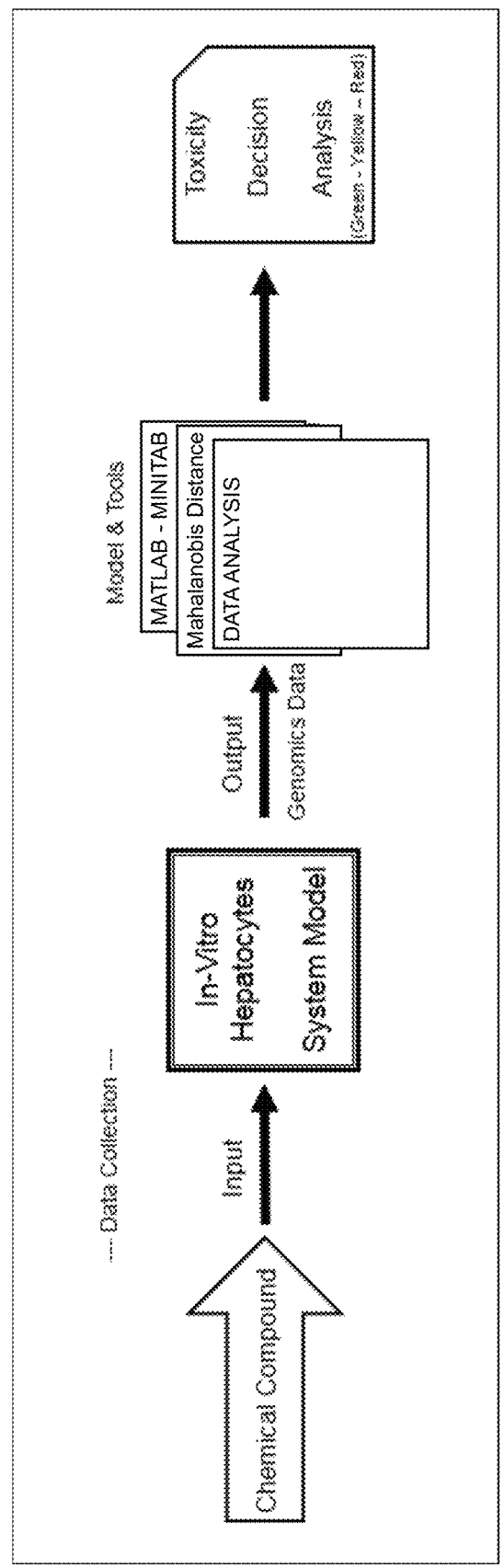
FIG. 7 is a flow diagram and illustrates a simplified Hepatocyte Toxicogenomics Evaluation System.

TmRNA is extracted from hepatocyte cell samples prepared for microarray analysis by PCR-based amplification (Hardiman 2004). A fluorescent dye (or biotin for Affymetrix microarrays) is incorporated into the amplified RNA sequences. Two-color arrays involve fluorescently labeling paired samples (control versus experimental) with different dyes (see FIG. 2-3). The amplified, labeled sequences, termed "targets," are then hybridized to the microarrays. After hybridization and washing, the arrays are imaged, e.g. with a confocal laser scanner or a two-photon laser microscope, and the relative fluorescence intensity (or streptavidin-conjugated phycoerythrin) for each gene-specific probe represents the expression level for that gene. The actual value reported depends on the microarray technology platform used and the experimental design. For Affymetrix GeneChips, in which each sample is hybridized to an individual array, expression for each gene is measured as an "average difference" that represents an estimated expression level, less nonspecific background. For two-color arrays, assays typically compare paired samples and report expression as the logarithm of the ratio of the experimental sample to the control sample. Regardless of the approach or technology, the fundamental data used in all subsequent analyses are the expression measures for each gene in each experiment. These expression data are typically represented as an "expression matrix" in which each row represents a particular gene and each column represents a specific biologic sample. In this representation, each row is a "gene expression vector," where the individual entries are its expression levels in the samples assayed and each column is a "sample expression vector" that records the expression of all genes in that sample.

Establishing a Framework & Risk Analysis Methodology

In one aspect, the invention requires collection of human hepatocyte (liver cell) transcriptomics data. Transcriptomics is the study and analysis of RNA produced by the genome of the cell, a mirror image of the DNA. By using this data, the invention evaluates the effect of chemical exposure on the cells by determining the amount of stress the cells are experiencing and provide the framework for risk.

The invention leverages mahalanobis distance and multidimensional DNA data from human hepatocytes along with the use of Matlab, Excel, and Minitab to evaluate the exposure data in order to build a risk framework. The invention was verified using laboratory collected multivariate DNA data, namely verifying from a known DNA response that occurs when hepatocytes are exposed to a ligand or chemical compound, e.g. GW7647.

Data Collection

In one embodiment, four human donors were used to provide four independent cell lines of hepatocytes. These hepatocytes were exposed to a chemical compound in-vitro at numerous times of exposure and concentrations that resulted in 120 different experiments, of which 20 formed a baseline of unstressed cells (normal group) and 100 formed a baseline of stressed cells (abnormal group).

Microarray-based transcriptomics were used to identify statistically significant genes that were either up or down-regulated from the 14,000 genes examined by micro-array analysis.

In one embodiment, all 14,000 genes are used on a Micro Array Transcriptomics Chip, see e.g. Affymetrix GeneChip. In another embodiment, a smaller sample of genes may be selected on the Micro Array Transcriptomics Chip to provide faster results by requiring less scanning time, and less processing to remove data errors.

In one non-limiting example, 192 genes were identified that were of significance and exhibited a reaction to a test ligand, e.g. GW7647. A number of the 192 genes were analyzed using more than one probe and as a result there were 465 different measurements or variables for each experiment. Over 80% showed up-regulation. Additionally, a majority of the 192 genes that showed up-regulation are known targets of PPARα binding. PPARα are nuclear receptor proteins of the hepatocyte that regulate gene expression through transcription factors and are essential in the regulation of lipid metabolism. Thus, a majority of the up-regulated genes encompass many pathway genes responsible for lipid metabolism.

Toxicity Risk Modeling Using Mahalanobis Distance (MD)

Mahalanobis distance (MD) is leveraged herein as the model that will feed into the risk evaluation of a particular compound. MD is a pattern comparison system that calculates a single measurement that describes the amount of divergence from the mean of the data by considering the correlation between the variables. It is a process of distinguishing one group from another or an abnormal group from a normal group.

In embodiments, where there are large number of variables, e.g. 40,000, 14,000, 465, 192, 100, 50, 20, or 10, MD provides an extremely sensitive method for detecting inter-variable changes from the reference data because it takes into account the variance of the multivariate data in each direction and it takes into account the correlation between the different variables or gene measurements. This allows for a more sensitive analysis in detecting any change among the different variables being measured in order to determine a normal or abnormal experiment from the reference/baseline data. The reference group (Normal group) is referred to as the Mahalanobis Space because it contains the baseline data that are in a normal state to which other collected data will be compared. The reference data set contains the mean, standard deviation, and correlation matrix of the variables in the normal data set. Normal in this case is considered healthy hepatocyte DNA that has not been exposed to any chemical compound. This baseline data may in some embodiments, be supplied as a library within the Micro Array Chip transcriptomics system.

Mahalanobis Distance

The MD is calculated as follows (Taguchi & R. Jungulum, 2002):

$$MD_j = D_j^2 = Z'_{ij} C^{-1} Z_{ij}, \text{ and} \quad \text{Equation 1:}$$

$$Z_{ij} = (X_{ij} - m_i)/s_i \quad \text{Equation 2:}$$

$X_{ij}$=value of the ith characteristic (gene) of the jth observation (experiment)
$m_i$=mean of the ith characteristic (gene)
$s_i$=standard deviation of the ith characteristic (gene)
$Z_{ij}=(z_{1j}, z_{2j}, z_{3j}, \ldots, z_{kj})$ standardized vector of the standardized values of the $X_{ij}$
$Z_{ij}'$=transpose of the $Z_{ij}$ standardized vector
$C^{-1}$=inverse of the correlation matrix
k=total number of gene measurements (e.g. 465 variables).

Equation 1 uses matrix/vector algebra to determine the MD number. It is based on the data's mean and variance for each variable and the correlation matrix of all the variables. In simplest of terms, Equation 2 standardizes the data and finds the center of mass of all the data points while the correlation matrix in Equation 1 determines the shape of how the data is distributed in the Mahalanobis space (MS). The shape of the MS would look like an ellipse in two dimensional space and would describe the amount of variability in a particular direction from the center of mass as shown in FIG. 13.

The MS is composed of the mean vector, standard deviation vector and correlation matrix of the data. Once the MS is determined, Equation 1 can be used to calculate if a randomly selected test point is within the MS. If the test point is within the MS there is a high probability that it is part of the group because it is within the standard deviation from the center of mass of the normal data group. Otherwise, if it is outside the MS it is considered not part of the group. The further away from MS the more significantly different the test point is from the center of mass and the normal group and the larger the calculated MD number.

It should be noted that genomics data can be highly correlated or multi-collinear across the many different variables and as a result the correlation matrix can approach singularity. Singularity means the matrix has a determinant of zero and the inverse correlation matrix will be undefined. As a result, the correlation matrix needs to be handled in such a manner as to ensure that the inverse correlation matrix is not undefined or inaccurate. In order to handle this multicollinearity of the data, the inverse correlation matrix can be computed by using the adjoint matrix or by using the Moore-Penrose pseudo inverse function (Barata & and Hussein, 2012). The Moore-Penrose pseudo inverse function has been widely used in data analysis applications especially in dealing with a non-square matrix. The MD number is calculated in different stages:

Stage I: Construction of the Mahalanobis Space and Measurement Scale

Data must be collected to identify the reference group from the unstressed cells. This data will be used to build the MS. The MS will be determined by the normal group's mean and standard deviation vector, and the correlation matrix. The reference group will be referred to as the healthy/normal group. This is the most important aspect of the approach, as this MS will be the reference point in n-space. It is used to compare stressed hepatocyte data collected from the perturbed experiments. The measurement scale extends from the centroid of the MS and is typically one unit distance away. The centroid of the MS is the zero point for the measurement scale. The larger the Mahalanobis distance (MD) number the further it is from the centroid of the Mahalanobis space and the higher the risk from exposure. The Mahalanobis distance for each perturbed experiment will be derived from information describing the MS and will be shown below. The MD is a value that describes the relationship between the normal group and the experiment. As hepatocyte cells are stressed by varying concentrations and times of exposure, the same variables that were measured to establish the MS for the normal group will be used to determine a MD number for the experimental data. This MD number should be much higher than the reference group if the results of the experiment are significantly different. This MD number will be indicative of the experiments generalized distance from the centroid of the healthy/normal group. As concentration and time of exposure increases the MD number for that experiment could increase or decrease, depending on whether the stress of the genes are increasing or decreasing. In general, unstressed hepatocytes tend to look quite similar to the healthy/normal group, while stressed hepatocytes tend to look quite different from the healthy/normal group and will have a higher MD number. In addition, the changes in correlation structure among the stressed hepatocytes strongly affect the MD number. In the case where a hepatocyte's MD number reaches a predetermined high threshold value, genes may start to mutate rapidly. If the MD number becomes similar to those of the healthy/normal group, the risk associated to exposure by a particular compound could be considered a low risk from exposure.

Construction of Normal

Referring now to FIG. 14, in one embodiment, 20 different experiments were conducted to build the healthy/normal group where the cells were not exposed to chemical, e.g. GW7647. FIG. 14 is an illustration of a snapshot of the database of Normal Unexposed Observation Data where the transcriptomics data of four cell lines—1153, 1154, 1156, and 1164—are provided across five time periods—2, 6, 12, 24, and 72 hours.

This baseline information is used to determine the amount of stress the exposed cells are experiencing from the reference cell pattern of unstressed cells—the healthy/normal group. All the data collected in the 120 different experiments and 465 variables, used the same units of measure consistent with measuring differential gene expression data. During gene expression, the gene will produce gene products either as RNA or proteins and the amount of this product will be measured to determine how active the gene is. This is measured using log-base 2 in order to maintain symmetry and unbias between up and down-regulated genes, and accommodate several magnitudes of differential gene expression folding, e.g., a two fold increase or decrease in gene activity. Next, the MD number for the reference experiments needs to be calculated to determine the baseline of the measurement scale that will be used to ascertain the risk threshold level.

The following is a simplistic example to show how to derive the Mahalanobis space and calculate the MD number for a given normal and abnormal group.

Referring now to FIG. 15, a centroid-standardized matrix is prepared.

Step 1: Form a Normal Data Set Centered Around (0,0)
a) Determine a group of normal measurements that will make up the normal group.
b) Calculate the mean, variance and standard deviation for each of the column variables (width & length).
c) Calculate the centroid of the normal data by computing the standardized values using the appropriate mean and standard deviation for the given variable. This causes the normal data set to be centered around (0, 0).

In this non-limiting embodiment, the normal data set for the hepatocyte experiments are the four different human liver cell lines that are exposed to 0 μM of concentration over the varying times—2, 6, 12, 24, and 72 hours. In other embodiment, a single cell line may be used. In another embodiment, this data is pre-loaded as a data set within the Chip System.

The centroid matrix in FIG. 15 is a standardized matrix that is calculated from the 20 normal measurements conducted by transcriptomics. The measurements of the 192 individual genes were conducted without any exposure to the GW7647 concentrate. The average down or up-regulation—the process by which a cell decreases or increases the quantity of cellular components such as RNA or proteins in response to an external stress—for each measured gene along with its standard deviation were calculated in order to standardize all the data into one common picture of the hepatocytes.

Referring now to FIG. 16, this shows the result of transposing the centroid matrix above in order to conduct a matrix operation.

Step 2: Derive the Mahalanobis Space
1. Calculate the correlation matrix of the normal data and note the mean and standard deviation of each variable from the normal data.
2. Calculate the inverse correlation matrix of the normal data.

Step 3: Derive Mahalanobis Distance for Normal Group
1. Multiply the transpose of the standardized matrix by the inverse correlation matrix.
2. Multiply the result by the standardized matrix in order to derive the MD for each normal data point.

This mean value will be used as a baseline to compare against each MD number of the abnormal data. This will determine if the test data's MD values are within the normal group or outside the normal group and by what magnitude of variability the abnormal data is different. This similar approach is used below to derive the MD number of the hepatocyte experiments for the normal data set.

Referring now to FIG. 17, the Mahalanobis Space (MS) (Normal) defines the mean, standard deviation, and correlation matrix along with the inverse correlation matrix that describes the structure and internal relationships of the genes in the normal group. It provides a mathematical picture of the inner workings, activity, signaling, and mechanisms of all the measured genes. The derivation of the MS is necessary in order to perform the proper calculations on the abnormal dataset.

Abnormal/Exposed Observations

Referring now to FIG. 18, an illustration of a snapshot of a dataset (perturbed) representing the abnormal group is calculated.

Step 4: MD of Experimental Observations/Abnormal Data
1. Analyze the experimental test data against the MS to determine if the data is within or outside the normal group. First, the abnormal data set is standardized using the mean and standard deviation from the original Mahalanobis space. This will help derive the centroid matrix for the abnormal data.
2. Multiply the transpose of the standardized matrix by the inverse correlation matrix. This result will then be multiplied by the standardized matrix in order to derive the MD number for each abnormal data point.

The calculations described in step 4 for this simple example are used to derive the MD number for the varied times and concentrations (Times: 2 hrs, 6 hrs, 12 hrs, 24 hrs, & 72 hrs; Concentrations: 0 μM, 0.001 μM, 0.01 μM, 0.1 μM, 1 μM, & 10 μM) of the hepatocyte experiments or abnormal group.

FIG. 18 shows a snapshot of a database having an abnormal group that consists of 100 observations and 465 gene variables and measurements (AADAC to ZNF423). These data reflects the different perturbations from the different times of exposure and concentration levels of exposure. The mean, the variance, and the standard deviation from the normal group and also shown in the MS is used to standardize the abnormal dataset. The centroid of the abnormal group is shown in FIG. 19 and reflects the different perturbations of stressed genes for the four different human hepatocyte cell lines—Hu1153, Hu1154, Hu1156, and Hu1164. The centroid matrix for the abnormal dataset is transposed as shown in FIG. 20 in order to be used in the matrix calculation Step 5: Analysis of Experimental Observations Verses Normal Group Determine if the MD number for the abnormal data is within or outside the normal group or MS. In relation to the MD baseline for the normal group, it is verifying that the MD number for the abnormal data points are not within the normal group. FIG. 13 depicts in 2D Mahalanobis space the cluster of normal data points within the solid ellipse line that represents the 1.86 MD baseline. The further the abnormal data points are from the center of the cluster the larger the MD number indicating the amount of difference a particular data point is from the normal group. It also depicts the amount of variability in a given direction as noted by the arrows. Movement along the longer arrow's direction indicates a larger amount of variability while movement along the shorter arrow's direction depicts a lesser amount of variability from the normal group. A similar analysis is performed on the hepatocyte data in Section 4—Hepatocyte Analysis. A 2D MS figure is not possible in the analysis for the hepatocyte data because the Mahalanobis space resides in 465 dimensional space due to the large number of variables being analyzed.

FIG. 19 shows an illustration of a snapshot of a centroid dataset of the abnormal group and reflects the different perturbations of stressed genes for the four different human hepatocyte cell lines—Hu1153, Hu1154, Hu1156, and Hu1164. FIG. 20 is an illustration of a snapshot of a centroid matrix for the abnormal dataset is transposed in order to be used in the matrix calculation as was described previously.

MD Calculation for Exposed Cell Lines

Once all the proper matrix calculations were performed as described above, the MDs were computed for each of the perturbed experiments (varying time and concentration) using the correlation matrix from the healthy/normal group. FIG. 21 shows the MD results for human cell lines 1153. The data in the table shows that as the time and concentration of GW7647 increases the MD number also increases. This response is due to additional stress the hepatocyte system is experiencing from GW7647 exposure. Likewise, FIG. 21 shows the results for human cell line 1154. The data in the table also reflects a similar result as the previous cell line. As the concentration increases or time of exposure increases, the MD number will also increase. There are occasions were the MD number may decrease from the previous lower concentration or exposure time and this could be explained by the fact that the hepatocytes are managing to metabolize the compound without much stress from exposure and are starting to return to a homeostasis state or the value is not significantly different than the normal group. FIG. 21 also shows very similar results as described above for human cell line 1156 and 1164.

Referring now to FIG. 22, mean MDs from the four different human cell lines (1153, 1154, 1156, 1164) were computed for each of the perturbed experiments (varying time and concentration) and the results are shown in FIG. 22. The average MD number for the four human cell lines also increase as a result of increased exposure and concentration of GW7647. FIG. 22 shows that at 72 hours of exposure from a concentration of 10 µM of GW7647, the MD number is 151.76, which is 8.4 times higher than the baseline MD number of 18.05. This indicates a major stress response from the evaluated gene due to exposure from GW7647.

Small Sample Size Analysis

Referring now to FIG. 23 which is an illustration of a snapshot of a database of a reduced sample set that probed only 10 genes across four cell lines across five time periods—2, 6, 12, 24, 72 hours—and five concentrations—0.001, 0.01, 0.1, 1.0, and 10.0 micromolar—was also observed and subjected to MD analysis.

Referring now to FIG. 24, the mean MDs from the four different human cell lines (1153, 1154, 1156, 1164) were computed for each of the perturbed experiments (varying time and concentration), and the results are shown in FIG. 24. The average MD number for the four human cell lines also increase as a result of increased exposure and concentration of GW7647.

Dose and Stress Response

Referring now to FIG. 25, it shows the MD number and p-value at a level of significance of 0.05 for the different concentration levels of exposure from GW7647 versus the different exposure times. The un-shaded portion of the table represents perturbations that did not have a level of significance that differentiated them from the unstressed hepatocytes. The shaded portion of the table represents perturbations that did have a level of significance that differentiated them from the unstressed hepatocytes. Thus, from FIG. 25 the threshold levels can be easily identified. The threshold level is the minimum value at which a significant response is discernable. In this case, it represents the minimum time of exposure and concentration level that induces the hepatocytes to indicate a level of abnormal stress and start to move to a new homeostasis state. The threshold level at 2 hours of exposure is at a concentration level of 1 µM. The threshold level at 6 hours of exposure is at a concentration level of 0.1 µM. The threshold level at 12, 24 and 72 hours of exposure is at a concentration level of 0.1 µM. The higher the concentration level and the longer the exposure time as shown in the table, the larger the MD number, indicating that the hepatocytes are experiencing an increased level of stress that could result in harm to the liver and other parts of the human body.

Referring now to FIG. 26, it shows the exposure time versus the concentration level. The un-shaded portion of the table represents perturbations that did not have a level of significance that differentiated them from the unstressed hepatocytes. The shaded portion of the table represents perturbations that did have a level of significance that differentiated them from the unstressed hepatocytes. Thus, FIG. 26 the threshold levels can be easily identified. The threshold level is the minimum value at which a significant response is discernable. In this case, it represents the minimum time of exposure and concentration level that induces the hepatocytes to indicate a level of abnormal stress and start to move to a new homeostasis state. The threshold level at 0.001 µM of concentration is at an exposure time greater than 72 hours. In order to verify if there is a threshold level at this concentration level, additional experiments would need to be conducted. It could also indicate that there is not a threshold level at 0.001 µM of GW7647 concentration. The threshold level at 0.01 µM of concentration is at an exposure time greater than 72 hours. This result is similar to the analysis from the previous concentration level. The threshold level at 0.1 µM of concentration is at an exposure time of hours. The threshold level at 1 µM and 10 µM of concentration is at an exposure time of 2 hours. The longer the exposure time and the higher the concentration level as shown in the table, the larger the MD number, indicating that the hepatocytes are experiencing an increased level of stress that could result in harm to the liver and other parts of the human body.

Toxicity Exposure Threshold

Referring now to FIG. 27, it provides a summary of the p-values for the MD number at the different times and concentration levels. Most of the MD numbers are significant, the exceptions being the ones shaded in gray with a p-value greater than 0.05 or less than the MD baseline of 18.05 for the healthy group. These occur mainly at concentration levels of 0.001 µM and 0.01 µM of exposure. Because the insignificant values are at concentration levels of 001 µM and 0.01 µM, this implies that the cells are able to metabolize GW7647 efficiently and show no significant difference in stress than the liver cells that were not exposed to GW7647.

Referring to FIG. 28, it shows a 95% confidence interval for each perturbation. The shaded portion of the table signifies that those concentrations and times do not show a significant level of gene activity to differentiate them from normal activity that the hepatocytes would experience when not exposed to GW7647.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims.

Having thus described the invention with the details and particularity required by the patent laws, what is claimed and desired protected by Letters Patent is set forth in the appended claims:

1. A system for high-throughput toxicity screening of a chemical, comprising:
   a transcriptomics Micro Array Chip with affixed Probes;
   a Micro Array Chip Scanner;
   a Micro Array Chip Fluidics Station;
   a Micro Array Chip Hybridization Oven; and
   a System software, wherein the system software comprises computer program instructions readable on a processor for performing transcriptomics steps on hepatocyte cells comprising:
   extracting mRNA from the hepatocyte cells exposed to the chemical, wherein the hepatocyte cells are exposed to at least five different concentrations of the chemical ranging from 0.001-10 micromolar to form at least five concentration samples, and each concentration sample of the five different concentration samples is exposed to the chemical for at least five different time periods ranging from 2-72 hours to form at least 25 concentration-duration samples;
   reverse transcribing the mRNA to cDNA;
   transcribing the cDNA to biotin-labelled cRNA;
   fragmenting the biotin-labelled cRNA;
   hybridizing the fragmented biotin-labelled cRNA to the transcriptomics Micro Array Chip;
   Washing and Staining the Hybridized MicroArray; and
   Scanning and Quantitating Scan Results of the at least 25 concentration-duration samples; and
   a Mahalanobis Distance software module operatively associated with the system software wherein the Mahalanobis Distance software module comprises computer program instructions readable on a processor for performing Mahalanobis Distance analysis of the Scan Results, and Displaying a 3-derivation Grid of toxicity of the chemical over the range of concentrations and exposure time periods.

2. A method of using the system of claim 1 for displaying toxicity of a chemical, comprising the steps:
   Providing the system of claim 1 and Performing a transcriptome array analysis of the hepatocyte cells exposed to the chemical;
   inputting Scan Results from the transcriptome array analysis into the Mahalanobis Distance software module and Calculating an Abnormal Mahalanobis Distance Value and a Abnormal p-value for each concentration-duration sample of the at least 25 concentration-duration samples of the hepatocyte cells;
   Calculating an Mahalanobis Distance number for 1-risk deviation, 2-risk deviations, and 3-risk deviations from a Normal Mahalanobis Distance, where the Normal Mahalanobis Distance is calculated from a transcriptome array analysis of hepatocyte cells unexposed to the chemical;
   Visually displaying the Abnormal Mahalanobis Distance Values on a grid of chemical concentrations against times of exposure, where the chemical concentrations are the at least five different concentrations of the chemical ranging from 0.001-10 micromolar and the times of exposure are the at least five different time periods ranging from 2-72 hours; and,
   Visually marking the grid of Abnormal Mahalanobis Distance Values to identify the 1-risk deviation, 2-risk deviations, and 3-risk deviations from Normal Mahalanobis Distance, wherein the marking of the 1-risk deviation, 2-risk deviations, and 3-risk deviations displays toxicity of a chemical over the range of concentrations and exposure time periods.

3. The method of claim 2, wherein the at least five different concentrations of the chemical ranging from 0.001-10 micromolar comprise 0.001, 0.01, 0.1, 1.0, and 10.0 micromolar.

4. The method of claim 2, where the at least five different time periods ranging from 2-72 hours comprise 2, 6, 12, 24, and 72 hours.

5. A method of using the system of claim 1 for obtaining a toxicity value for a chemical compound, comprising the steps:
   administering the chemical compound to human hepatocytes in an in-vitro microassay having a plurality of sample wells;
   Exposing the hepatocytes to the compound for at least two or more different time periods and at two or more different concentrations;
   Forming a selection of a baseline of unstressed normal cells using a selection of the hepatocytes having an exposure time of 0 and a concentration of 0;
   Forming a selection of a baseline of stressed abnormal cells using a selection of hepatocytes having an exposure time greater than 0 and a concentration of greater than zero;
   providing the system of claim 1 and obtaining Scan Results data from the baseline of normal cells and the baseline of abnormal cells by identifying statistically significant up-regulated or down-regulated genes in the hepatocytes using two or more RNA-ligand probes;
   using the Mahalanobis Distance software module to calculate a Normal Mahalanobis Value using Scan Results data from the baseline of normal cells using Equation 1 and Equation 2 below:

$$MD_j = D_j^2 = Z'_{ij} C^{-1} Z_{ij} \quad \text{Equation 1}$$

$$Z_{ij} = \frac{X_{ij} - m_i}{s_i} \quad \text{Equation 2}$$

Xij=value of the ith characteristic (gene) of the jth observation (experiment)
mi=mean of the ith characteristic (gene)
si=standard deviation of the ith characteristic (gene)
Zij=(z1j, z2j, z3j, . . . , zkj) standardized vector of the standardized values of the Xij
Zij' transpose of the Zij standardized vector
C−1=inverse of the correlation matrix
k=total number of gene measurements (n variables), and
   using the Mahalanobis Distance software module to calculate an Abnormal Mahalanobis Value using Scan Results data from the baseline of abnormal cells using Equation 1 and Equation 2; and
   using the Mahalanobis Distance software module to calculate a Toxicity Risk Ratio by dividing the Normal Mahalanobis Value by the Abnormal Mahalanobis Value.

6. The method of claim 5, wherein the hepatocytes comprise two or more samples of hepatocytes, each sample obtained at a different time or from a different location than the other.

7. The method of claim 5, wherein the hepatocytes comprise at least four samples of hepatocytes, each sample obtained at a different time or from a different location than the other.

8. The method of claim 5, wherein the step of exposing the hepatocytes to the compound for at least two or more different time periods comprises exposing the hepatocytes to the compound for five time periods defined as 2, 6, 12, 24, and 72 hours.

9. The method of claim 5, wherein the step of exposing the hepatocytes to the compound at two or more different concentrations comprises exposing the hepatocytes to the compound at six different concentrations defined as 0.0, 0.001, 0.01, 0.1, 1.0, 10.0 micro Moles.

10. The method of claim 5, wherein the step of obtaining Scan Results data from the baseline of normal cells and the baseline of abnormal cells by identifying statistically significant up-regulated or down-regulated genes in the hepatocytes using two or more RNA-ligand probes comprises using at least five RNA-ligand probes.

11. The system of claim 1, comprising:
    (i) human hepatocytes in an in-vitro microassay having a plurality of sample wells;
    (ii) an RNA-ligand kit comprising two or more RNA-ligands, and sufficient reagents, buffers, capture agents, detection complexes, instructions, enzymes or polymerases, nucleic acids or fragments, and containers for obtaining transcriptomics data from the baseline of normal cells and the baseline of abnormal cells by identifying statistically significant up-regulated or down-regulated genes in the hepatocytes using two or more RNA-ligand probes; and
    (iii) means provided by the system of claim 1 for quantifying up-regulation or down-regulation of genes in hepatocytes.

* * * * *